(12) United States Patent
Yamasaki et al.

(10) Patent No.: US 8,078,409 B2
(45) Date of Patent: Dec. 13, 2011

(54) EXTERNAL QUALITY CONTROL METHOD, EXTERNAL QUALITY CONTROL COMPUTER, PREPROCESSING DEVICE, AND NUCLEIC ACID DETECTING DEVICE

(75) Inventors: Masatoshi Yamasaki, Sanda (JP); Keiji Fujimoto, Kobe (JP)

(73) Assignee: Sysmex Corporation, Hyogo (JP)

( * ) Notice: Subject to any disclaimer, the term of this patent is extended or adjusted under 35 U.S.C. 154(b) by 1260 days.

(21) Appl. No.: 11/491,912

(22) Filed: Jul. 25, 2006

(65) Prior Publication Data
US 2007/0027635 A1 Feb. 1, 2007

(30) Foreign Application Priority Data

Jul. 26, 2005 (JP) .................................. 2005-215937

(51) Int. Cl.
*C12Q 1/68* (2006.01)
*G01N 33/48* (2006.01)
(52) U.S. Cl. ................................. 702/19; 435/6; 702/20
(58) Field of Classification Search .................. None
See application file for complete search history.

(56) References Cited

U.S. PATENT DOCUMENTS

| | | | |
|---|---|---|---|
| 5,846,489 A | 12/1998 | Bienhaus et al. | |
| 6,410,278 B1 | 6/2002 | Notomi et al. | |
| 6,562,568 B1 | 5/2003 | Kleiber et al. | |
| 6,629,060 B2 | 9/2003 | Okuno et al. | |
| 7,572,638 B2 * | 8/2009 | Pressman et al. | 436/47 |
| 2005/0042138 A1 | 2/2005 | Ueda et al. | |

FOREIGN PATENT DOCUMENTS

WO 97/10365 * 3/1997

* cited by examiner

*Primary Examiner* — Shubo Zhou
(74) *Attorney, Agent, or Firm* — Sughrue Mion, PLLC

(57) ABSTRACT

An external quality control method, using an external quality control system which comprises an external quality control computer and a plurality of preprocessing devices connected to the external quality control computer via a network, comprising: performing preprocessing operations on preprocessing quality control samples, the preprocessing devices being adapted to prepare samples for measurement of target nucleic acid; measuring preprocessed preprocessing quality control samples to obtain measurement data; providing the measurement data to the external quality control computer over the network; storing the measurement data; and implementing an external quality control process based on the measurement data, is disclosed. An external quality control method for detection of nucleic acid, an external quality control method for preparation of calibration curve, an external quality control computer, a preprocessing device, and a nucleic acid detecting device are also disclosed.

8 Claims, 34 Drawing Sheets

Fig.8

| CK19 copies/$\mu$L | Discrimination |
|---|---|
| $\leq 250$ | ND |
| $250 - 5 \times 10^3$ | + |
| $> 5 \times 10^3$ | ++ |

Fig.13

Contents of absorbance measurement data transmitted to server 1 from personal computer 6

| Device ID | Lot number of pseudo tissue | Absorbance | Measuring time |
|---|---|---|---|
| 111 | 12345 | 0.225 | 2005/2/23 10:15 |

Fig.14

Contents of absorbance database DB1

| Device ID | Lot number of pseudo tissue | Absorbance | Measuring time |
|---|---|---|---|
| 111 | 12345 | 0.225 | 2005/2/21 10:15 |
| | | 0.227 | 2005/2/22 10:19 |
| | | 0.223 | 2005/2/23 10:18 |
| 112 | 12345 | 0.223 | 2005/2/21 11:15 |
| | | 0.228 | 2005/2/22 12:19 |
| | | 0.226 | 2005/2/23 10:18 |

Fig.15

Contents of absorbance statistical database DB2

| Date | Average | 1SD | 2SD | 3SD | Reference system measurement data |
|---|---|---|---|---|---|
| 2005/2/21 | 0.226 | 0.002 | 0.004 | 0.006 | 0.225 |
| 2005/2/22 | 0.227 | 0.003 | 0.006 | 0.009 | 0.224 |
| 2005/2/23 | 0.227 | 0.003 | 0.006 | 0.009 | 0.226 |

Contents of measurement data transmitted to sever 1 from personal computer 6

Fig.19A

| Device ID | Lot number of CK19 control | Rising time of CK19 (min) | Copy number of CK19 | Rising time of arabido | Measuring time |
|---|---|---|---|---|---|
| 111 | 33333 | 11.4 | 5.0E+03 | ND | 2005/2/23 11:15 |

Fig.19B

| Device ID | Lot number of Internal control (arabido control) | Rising time of CK19 (min) | Copy number of CK19 | Rising time of arabido | Measuring time |
|---|---|---|---|---|---|
| 111 | 33333 | ND | ND | 11.0 | 2005/2/23 11:15 |

Fig.19C

| Device ID | Lot number of calibrator C1 | Rising time of CK19 (min) | Copy number of CK19 | Measuring time |
|---|---|---|---|---|
| 111 | 33333 | 11.5 | 2.2E+03 | 2005/2/23 11:15 |

Fig.19D

| Device ID | Lot number of calibrator C2 | Rising time of CK19 (min) | Copy number of CK19 | Measuring time |
|---|---|---|---|---|
| 111 | 33333 | 10.4 | 3.4E+05 | 2005/2/23 11:15 |

Fig.19E

| Device ID | Lot number of calibrator C3 | Rising time of CK19 (min) | Copy number of CK19 | Measuring time |
|---|---|---|---|---|
| 111 | 33333 | 9.5 | 2.1E+07 | 2005/2/23 11:15 |

Fig.20A

Contents of quality control database DB3

| Device ID | Lot number of CK19 control | Rising time of CK19 (min) | Copy number of CK19 | Rising time of arabido | Measuring time |
|---|---|---|---|---|---|
| 111 | 33333 | 11.3 | 5.5E+03 | ND | 2005/2/21 12:15 |
| | | 11.2 | 8.7E+03 | ND | 2005/2/22 13:15 |
| | | 11.1 | 1.4E+04 | ND | 2005/2/23 11:15 |
| 112 | 33333 | 11.0 | 2.2E+04 | ND | 2005/2/21 13:15 |
| | | 11.2 | 8.7E+03 | ND | 2005/2/22 14:15 |
| | | 11.3 | 5.5E+03 | ND | 2005/2/23 15:15 |

Fig.20B

| Device ID | Lot number of Internal control (arabido control) | Rising time of CK19 (min) | Copy number of CK19 | Rising time of arabido | Measuring time |
|---|---|---|---|---|---|
| 111 | 33333 | ND | ND | 11.5 | 2005/2/21 12:15 |
| | | ND | ND | 11.0 | 2005/2/22 13:15 |
| | | ND | ND | 11.2 | 2005/2/23 11:15 |
| 112 | 33333 | ND | ND | 11.3 | 2005/2/21 13:15 |
| | | ND | ND | 11.2 | 2005/2/22 14:15 |
| | | ND | ND | 11.1 | 2005/2/23 15:15 |

Contents of quality control database DB3

Fig.21A

| Device ID | Lot number of calibrator C1 | Rising time of CK19 (min) | Copy number of CK19 | Measuring time |
|---|---|---|---|---|
| 111 | 33333 | 11.4 | 3.0E+03 | 2005/2/21 12:15 |
| | | 11.9 | 2.1E+03 | 2005/2/22 13:15 |
| | | 11.8 | 2.0E+03 | 2005/2/23 11:15 |
| 112 | 33333 | 11.7 | 2.7E+03 | 2005/2/21 13:15 |
| | | 11.9 | 2.1E+03 | 2005/2/22 14:15 |
| | | 11.5 | 2.4E+03 | 2005/2/23 15:15 |

Fig.21B

| Device ID | Lot number of calibrator C2 | Rising time of CK19 (min) | Copy number of CK19 | Measuring time |
|---|---|---|---|---|
| 111 | 33333 | 10.5 | 1.9E+05 | 2005/2/21 12:15 |
| | | 10.6 | 3.8E+05 | 2005/2/22 13:15 |
| | | 10.4 | 4.2E+05 | 2005/2/23 11:15 |
| 112 | 33333 | 10.7 | 2.2E+05 | 2005/2/21 13:15 |
| | | 10.5 | 3.6E+05 | 2005/2/22 14:15 |
| | | 10.4 | 2.9E+05 | 2005/2/23 15:15 |

Fig.21C

| Device ID | Lot number of calibrator C3 | Rising time of CK19 (min) | Copy number of CK19 | Measuring time |
|---|---|---|---|---|
| 111 | 33333 | 9.4 | 2.9E+07 | 2005/2/21 12:15 |
| | | 9.6 | 2.0E+07 | 2005/2/22 13:15 |
| | | 9.4 | 1.9E+07 | 2005/2/23 11:15 |
| 112 | 33333 | 9.6 | 2.7E+07 | 2005/2/21 13:15 |
| | | 9.4 | 2.1E+07 | 2005/2/22 14:15 |
| | | 9.4 | 2.3E+07 | 2005/2/23 15:15 |

Fig.22

Contents of quality control statistical database DB4 (a)

| Date | Object to be measured | Lot number | Measurement item | Average | 1SD | 2SD | 3SD | Reference measurement data |
|---|---|---|---|---|---|---|---|---|
| 2005/2/21 | CK19 control | 33333 | Rising time of CK19 | 11.3 | 0.1 | 0.2 | 0.3 | 11.4 |
| | | | Copy number of CK19 | 4.1E+03 | 2.6E+03 | 5.2E+03 | 7.9E+03 | 3.0E+03 |
| | Internal control (arabido control) | 33333 | Rising time of arabido | ND | — | — | — | ND |
| | | | Rising time of CK19 | ND | — | — | — | ND |
| | | | Copy number of CK19 | ND | — | — | — | ND |
| | Calibrator 1 | 33333 | Rising time of arabido | 11.2 | 0.1 | 0.2 | 03 | 11.2 |
| | | | Rising time of CK19 | 11.3 | 0.1 | 0.2 | 0.3 | 11.2 |
| | | | Copy number of CK19 | 4.1E+03 | 2.6E+03 | 5.2E+03 | 7.9E+03 | 3.0E+03 |
| | Calibrator 2 | 33333 | Rising time of CK19 | 10.5 | 0.1 | 0.2 | 0.3 | 10.4 |
| | | | Copy number of CK19 | 1.7E+05 | 9.7E+04 | 1.9E+05 | 2.9E+05 | 3.0E+03 |
| | Calibrator 3 | 33333 | Rising time of CK19 | 9.5 | 0.1 | 0.2 | 0.3 | 9.4 |
| | | | Copy number of CK19 | 3.7E+07 | 1.6E+07 | 3.2E+07 | 4.8E+07 | 3.0E+07 |

Fig.23

Contents of quality control statistical database DB4 (b)

| Date | Object to be measured | Lot number | Measurement item | Average | 1SD | 2SD | 3SD | Reference measurement data |
|---|---|---|---|---|---|---|---|---|
| 2005/2/22 | CK19 control | 33333 | Rising time of CK19 | 11.3 | 0.1 | 0.2 | 0.3 | 11.4 |
| | | | Copy number of CK19 | 5.0E+03 | 2.0E+03 | 4.0E+03 | 6.0E+03 | 3.0E+03 |
| | Internal control (arabido control) | 33333 | Rising time of arabido | ND | — | — | — | ND |
| | | | Rising time of CK19 | ND | — | — | — | ND |
| | | | Copy number of CK19 | ND | — | — | — | ND |
| | | | Rising time of arabido | 11.4 | 0.1 | 0.2 | 03 | 11.2 |
| | Calibrator 1 | 33333 | Rising time of CK19 | 11.4 | 0.1 | 0.2 | 0.3 | 114 |
| | | | Copy number of CK19 | 3.0E+03 | 2.0E+03 | 4.0E+03 | 6.0E+03 | 3.0E+03 |
| | Calibrator 2 | 33333 | Rising time of CK19 | 10.6 | 0.1 | 0.2 | 0.3 | 10.4 |
| | | | Copy number of CK19 | 1.8E+05 | 9.7E+04 | 1.9E+05 | 2.9E+05 | 3.0E+03 |
| | Calibrator 3 | 33333 | Rising time of CK19 | 9.6 | 0.1 | 0.2 | 0.3 | 9.4 |
| | | | Copy number of CK19 | 2.9E+07 | 1.7E+07 | 3.4E+07 | 5.1E+07 | 3.0E+07 |

Fig.24

Contents of quality control statistical database DB4 (c)

| Date | Object to be measured | Lot number | Measurement item | Average | 1SD | 2SD | 3SD | Reference measurement data |
|---|---|---|---|---|---|---|---|---|
| 2005/2/23 | CK19 control | 33333 | Rising time of CK19 | 11.1 | 0.1 | 0.2 | 0.3 | 11.1 |
| | | | Copy number of CK19 | 4.4E+03 | 2.6E+03 | 5.2E+03 | 7.9E+03 | 3.0E+07 |
| | Internal control (arabido control) | 33333 | Rising time of arabido | ND | — | — | — | ND |
| | | | Rising time of CK19 | ND | — | — | — | ND |
| | | | Copy number of CK19 | ND | — | — | — | ND |
| | | | Rising time of arabido | 11.2 | 0.1 | 0.2 | 03 | 11.2 |
| | Calibrator 1 | 33333 | Rising time of CK19 | 11.2 | 0.1 | 0.2 | 0.3 | 11.2 |
| | | | Copy number of CK19 | 2.5E+0.3 | 2.6E+03 | 5.2E+03 | 7.9E+03 | 2.5E+03 |
| | Calibrator 2 | 33333 | Rising time of CK19 | 10.4 | 0.1 | 0.2 | 0.3 | 10.4 |
| | | | Copy number of CK19 | 2.5E+05 | 9.7E+04 | 1.9E+05 | 2.9E+05 | 2.5E+05 |
| | Calibrator 3 | 33333 | Rising time of CK19 | 9.6 | 0.1 | 0.2 | 0.3 | 9.6 |
| | | | Copy number of CK19 | 2.5E+07 | 1.6E+07 | 3.2E+07 | 4.8E+07 | 2.5E+07 |

Analyte measuring processing in nucleic acid detecting device main unit

EXTERNAL QUALITY CONTROL METHOD, EXTERNAL QUALITY CONTROL COMPUTER, PREPROCESSING DEVICE, AND NUCLEIC ACID DETECTING DEVICE

FIELD OF THE INVENTION

The present invention relates an external quality control method for preprocessing, an external quality control method for detection of nucleic acid, an external quality control method for preparation of calibration curve, an external quality control computer, a preprocessing device, and a nucleic acid detecting device.

BACKGROUND

There is known a remote support system which collects measurement data of a quality control substance from a plurality of blood test devices in a server, tallies up the collected measurement data by the server, and allows a user of a blood test device to view the tallied result (see U.S. Pat. No. 6,629,060).

This remote support system enables a user of a blood test device to check whether the blood test device in the particular facility operates properly, namely to conduct a so-called external quality control by comparing measurement data obtained by measurement of quality control substances by blood test device installed in other facilities with measurement data obtained by measurement of a quality control substance by the blood test device in the particular facility.

There is also developed a nucleic acid detecting device which amplifies a nucleic acid contained in a sample and detects the amplified nucleic acid (see U.S. Pat. No. 5,846,489, and U.S. Pre-Grant Publication No. 2005-42138).

In such a nucleic acid detecting device, a preprocessing such as extraction of nucleic acid or homogenization of tissue is executed prior to placing a sample in the nucleic acid detecting device, and the sample having subjected to the preprocessing is placed in the nucleic acid detecting device where a target nucleic acid is detected after amplified by using a predetermined reagent.

Nucleic acid detecting devices are generally used in research uses, and in such uses, the necessity of quality control little arises, and especially no necessity arises for external quality control. In a conventional nucleic acid detecting device, only internal quality control using generated DNA or RNA as a quality control substance is attempted.

When a nucleic acid detecting device is used for clinical purposes such as for cancer diagnosis or infectious disease test, the detection result will significantly influence on the definitive diagnosis of infectious disease, cancer, genetic disorder and the like, so that the quality control is very important.

Especially in the case of cancer diagnosis or the like, it is required to derive a determination result providing reference for diagnosis, based on quantitative measurement data obtained in the nucleic acid detecting device. For example, when an analyte obtained from a patient during surgery of cancer is subjected to measurement by a nucleic acid detecting device, diagnosis of lymph node metastasis of the cancer is diagnosed, and a region of lymph node dissection is determined based on the diagnosis, the measurement data should be very accurate and reliable. Also rapidity is required for the case of intraoperative diagnosis.

A nucleic acid detecting process, however, needs more complicated processing like a preprocessing, compared to a blood test process, so that it was impossible to directly apply the external quality control employed in a conventional blood test to such a nucleic acid detecting process.

Particularly, in a nucleic acid detecting device, it is necessary to conduct a preprocessing such as extraction of nucleic acid or homogenization of tissue prior to placing a sample in the nucleic acid detecting device, and to place the sample having subjected to the preprocessing to the nucleic acid detecting device, as described above, however, such a preprocessing is executed in different manners in different facilities, and quality control for such preprocessing is not noticed at all. However, it is impossible to secure the reliability of the subsequent nucleic acid detecting process unless the reliability of preprocessing is secured.

SUMMARY

The scope of the present invention is defined solely by the appended claims, and is not affected to any degree by the statements within this summary.

A first aspect of the present invention is an external quality control method, using an external quality control system which comprises an external quality control computer and a plurality of preprocessing devices connected to the external quality control computer via a network, comprising: at the plurality of preprocessing devices, performing preprocessing operations on preprocessing quality control samples, the preprocessing devices being adapted to prepare samples for measurement of target nucleic acid; at the plurality of preprocessing devices, measuring preprocessed preprocessing quality control samples to obtain measurement data; at the plurality of preprocessing devices, providing the measurement data to the external quality control computer over the network; at the external quality control computer, storing the measurement data; and at the external quality control computer, implementing an external quality control process based on the measurement data.

A second aspect of the present invention is an external quality control method, using an external quality control computer, comprising: receiving, via a network, a plurality of measurement data obtained by measuring preprocessing quality control samples preprocessed by a plurality of preprocessing devices which are adapted to prepare samples for measurement of target nucleic acid; storing the measurement data; and implementing an external quality control process based on the measurement data.

A third aspect of the present invention is an external quality control method for detection of nucleic acid, using an external quality control system which comprises an external quality control computer and a plurality of nucleic acid detecting devices connected to the external quality control computer via a network, comprising: at the plurality of nucleic acid detecting devices, measuring nucleic acid quality control samples to obtain measurement data, the nucleic acid detecting devices being adapted to detect target nucleic acid; at the plurality of nucleic acid detecting devices, providing the measurement data to the external quality control computer over the network; at the external quality control computer, storing the measurement data; and at the external quality control computer, implementing an external quality control process based on the measurement data.

A fourth aspect of the present invention is an external quality control method for detection of nucleic acid, using an external quality control computer, comprising: receiving, via a network, a plurality of measurement data which indicate a quality of target nucleic acid detecting operation from a plurality of nucleic acid detecting devices which are adapted to detect target nucleic acid; storing the measurement data; and implementing an external quality control process based on the measurement data.

A fifth aspect of the present invention is an external quality control method for detection of nucleic acid, using an external quality control computer, comprising: receiving, via a network, a plurality of first measurement data obtained by measuring preprocessing quality control samples preprocessed by a plurality of preprocessing devices which are adapted to prepare samples for measurement of target nucleic acid; storing the first measurement data; implementing a first external quality control process based on the first measurement data; receiving, via the network, a plurality of second measurement data which indicate a quality of target nucleic acid detecting operation from a plurality of nucleic acid detecting devices which are adapted to detect target nucleic acid from samples preprocessed by the preprocessing devices; storing the second measurement data; and implementing a second external quality control process based on the second measurement data.

A sixth aspect of the present invention is an external quality control method for preparation of calibration curve, using an external quality control system which comprises an external quality control computer and a plurality of nucleic acid detecting devices connected to the external quality control computer via a network, comprising: at the plurality of nucleic acid detecting devices, measuring calibrators to obtain measurement data, the nucleic acid detecting devices being adapted to detect target nucleic acid and the calibrators being used for converting information of time taken until target nucleic acid are amplified up to predetermined amount to information of amount of the target nucleic acid; at the plurality of nucleic acid detecting devices, providing the measurement data to the external quality control computer over the network; at the external quality control computer, storing the measurement data; and at the external quality control computer, implementing an external quality control process based on the measurement data.

A seventh aspect of the present invention is an external quality control computer, connected to a network, for an external quality control of preprocessing operation performed before detection of nucleic acid, comprising: a receiver for receiving, via the network, a plurality of measurement data obtained by measuring preprocessing quality control samples preprocessed by a plurality of preprocessing devices which are adapted to prepare samples for measurement of target nucleic acid; a memory for storing the measurement data; and means for implementing an external quality control process based on the measurement data.

A eighth aspect of the present invention is an external quality control computer, connected to a network, for an external quality control of detection of nucleic acid, comprising: a receiver for receiving, via the network, a plurality of measurement data which indicate a quality of target nucleic acid detecting operation from a plurality of nucleic acid detecting devices which are adapted to detect target nucleic acid; a memory for storing the measurement data; and means for implementing an external quality control process based on the measurement data.

A ninth aspect of the present invention is a preprocessing device for performing preprocessing operations before detection of nucleic acid, comprising: a preprocessing section for performing preprocessing operations on preprocessing quality control samples, the preprocessing section being adapted to prepare samples for measurement of target nucleic acid; a measurement section for measuring the preprocessed preprocessing quality control samples to obtain measurement data; and a transmitter for transmitting measurement data to an external quality control computer via a network.

A tenth aspect of the present invention is a nucleic acid detecting device, comprising: a measurement section for measuring nucleic acid quality control samples to obtain measurement data, the measurement section being adapted to detect target nucleic acid; a transmitter for transmitting the measurement data to an external quality control computer via a network.

BRIEF DESCRIPTION OF THE DRAWINGS

FIG. 8 is a view showing correspondence between copy number and determination result.

FIG. 13 is a view showing contents of absorbance measurement data transmitted to the server 1 from the personal computer 6.

FIG. 14 is a view showing contents of absorbance database DB1.

FIG. 15 is a view showing contents of absorbance statistical database DB2.

FIGS. 19A through 19E are views showing contents of measurement data transmitted to the server 1 from the personal computer 6.

FIGS. 20A and 2B are views showing contents of quality control database DB3 (measurement data of control solution).

FIGS. 21A through 21C are views showing contents of quality control database DB3 (measurement data of calibrator).

FIG. 22 is a view showing contents of quality control statistical database DB4.

FIG. 23 is a view showing contents of quality control statistical database DB4.

FIG. 24 is a view showing contents of quality control statistical database DB4.

DETAILED DESCRIPTION OF THE PREFERRED EMBODIMENTS

The preferred embodiments of the present invention are described hereinafter with reference to the drawings.

First Embodiment

[Overall Structure of External Quality Control System]

Figure 1:
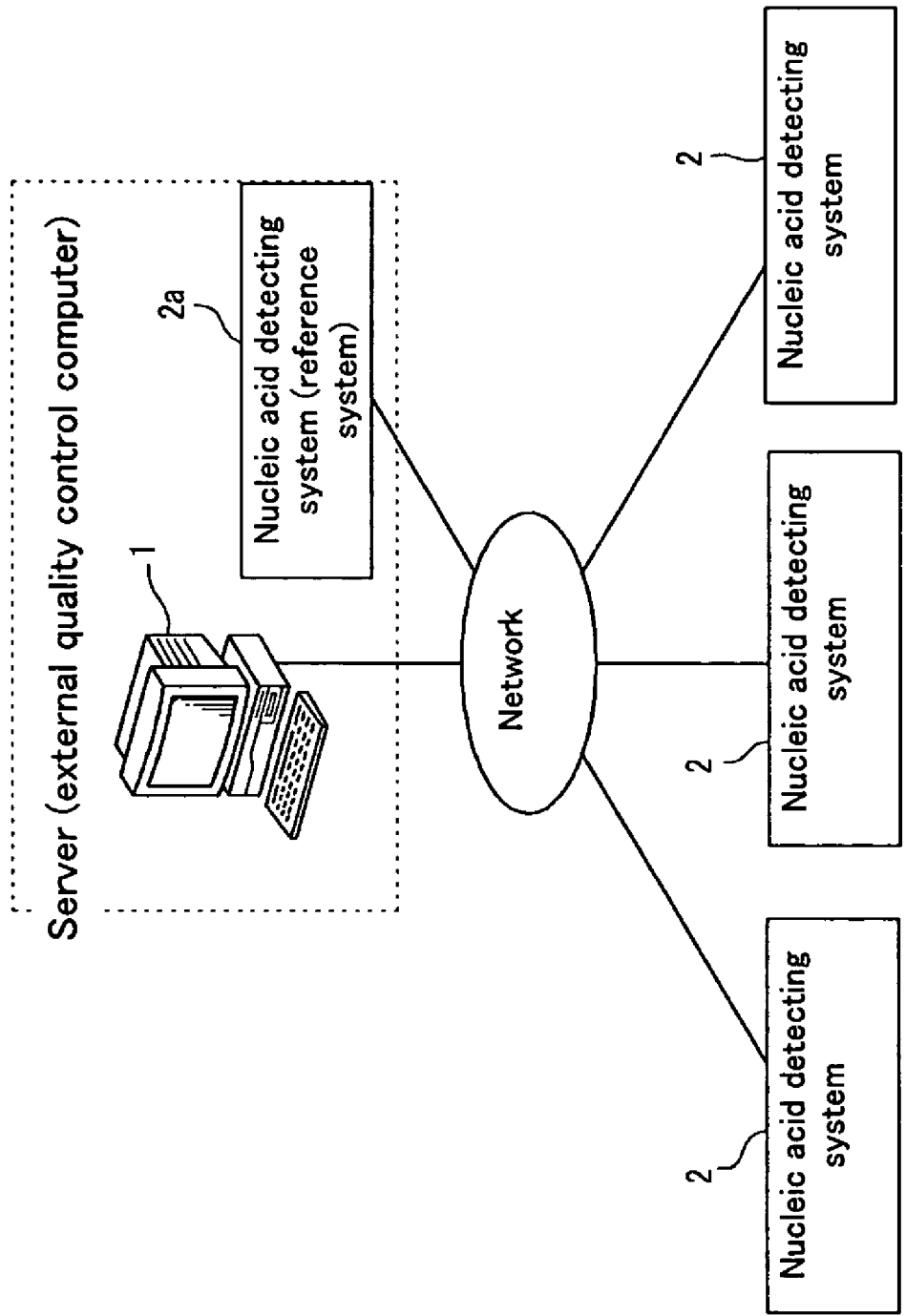
FIG. 1 is an overall structure view of an external quality control system.

FIG. 1 shows an overall structure of an external quality control system having an external quality control computer (hereinafter, simply referred to as "server") 1 and a plurality of nucleic acid detecting systems 2 connected to the server 1 via a network such as the Internet.

The server 1 is provided on the end of a quality control service provider, and the nucleic acid detecting system 2 is provided on the end of a user of the nucleic acid detecting system 2, for example, in a hospital. The server 1 and each of the nucleic acid detecting systems 2 are communicatable with each other via a network.

Also on the end of the service provider, a nucleic acid detecting system 2a serving as a reference system is disposed, and the reference system 2a is also connected to the server 1 via a network or directly to be communicatable with the server 1.

[Nucleic Acid Detecting System]

The nucleic acid detecting system (gene amplification detecting system) 2 according to the present embodiment is capable of outputting as measurement data concentration of target nucleic acid (target gene) contained in an analyte which may be a tissue excised from a living body (human body) such as lymph node.

More specifically, the nucleic acid detecting system 2 is used as a genetic diagnosis system for breast cancer lymph node metastasis, and determines concentration of target nucleic acid (cancer gene; mRNA) by measuring turbidity of solution occurring with amplification when a lymph node excised from human body (analyte) is subjected to a preprocessing (homogenization, extraction or the like) to prepare a solubilized extraction which is a measuring analyte for nucleic acid detection, and a target nucleic acid (target gene) existing in the measuring analyte is amplified by the LAMP method (Loop-mediated Isothermal Amplification/See U.S. Pat. No. 6,410,278).

The nucleic acid detecting system 2 is used for intraoperative rapid diagnosis, concretely during a surgery of breast cancer or the like. For example, the system 2 determines concentration of a gene originating from lymph node (target nucleic acid) from a lymph node excised during a surgery, and then a physician diagnoses the degree of cancer metastasis during the surgery with reference to the concentration and determines a region of lymph node dissection. Therefore, high reliability and rapidity are required for the output of the system 2.

Figure 2:
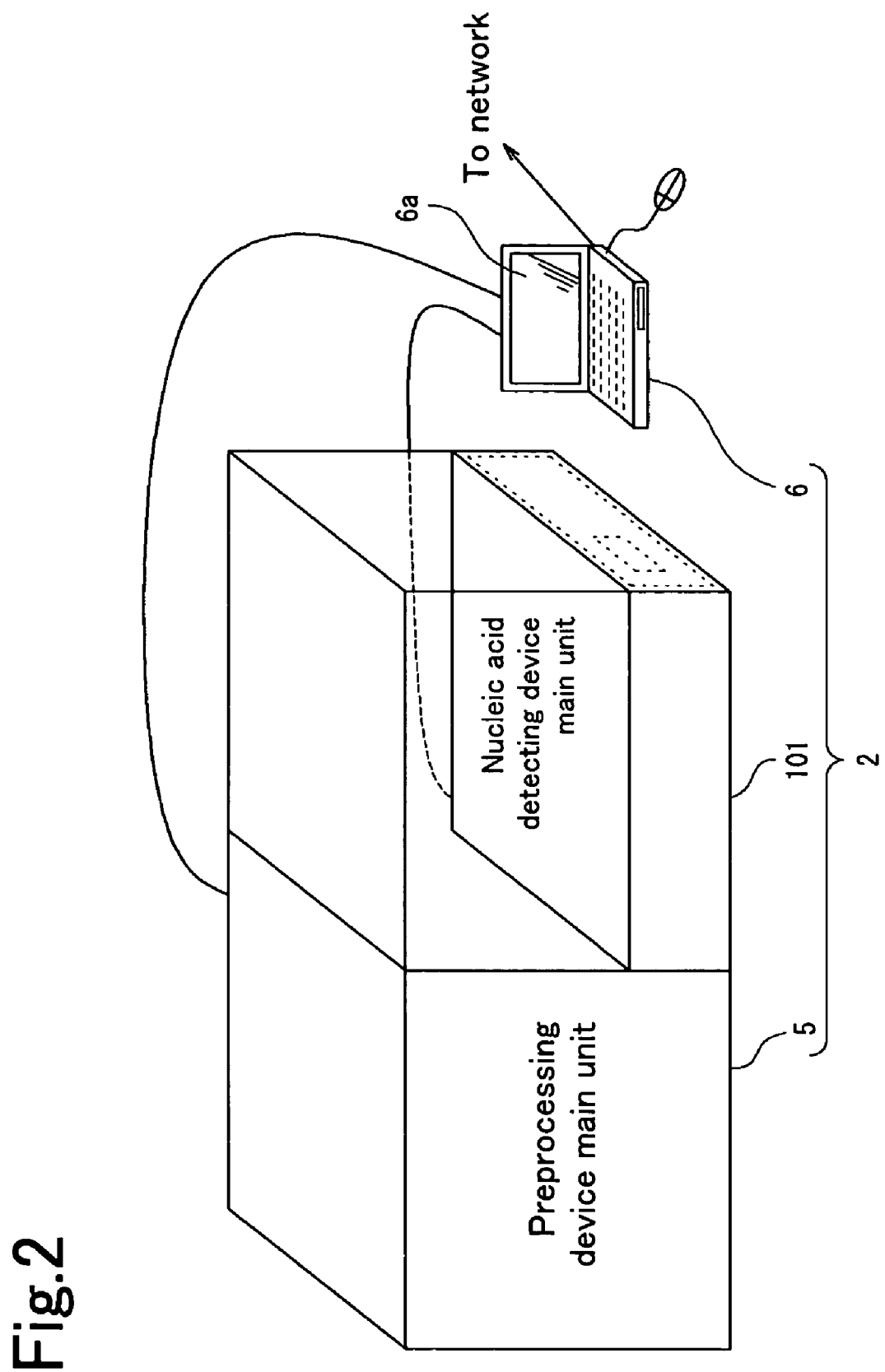
FIG. 2 is an overall structure view of a nucleic acid detecting system.

As shown in FIG. 2, the nucleic acid detecting system 2 has a preprocessing device main unit 5 for conducting a preprocessing such as homogenization on an analyte obtained from a human body or the like to prepare a measuring analyte, and a nucleic acid detecting device main unit 101 for detecting a target nucleic acid contained in the measuring analyte.

The nucleic acid detecting system 2 also has a personal computer 6 which is a data processing device for conducting data processing or data communication. The data processing device 6 also serves as a control device that receives measurement data from each of the preprocessing device main unit 5 and the nucleic acid detecting device main unit 101, and transmits an operation instructing signal or the like to the preprocessing device main unit 5 and the nucleic acid detecting device main unit 101. That is, the preprocessing device main unit 5 and the data processing device 6 embody the preprocessing device, and the nucleic acid detecting device main unit 101 and the data processing device 6 embody the nucleic acid detecting device.

The data processing device 6 is connected to a network, and capable of transmitting measurement data or the like transmitted from a respective transmitting unit of the preprocessing device main unit 5 or the nucleic acid detecting device main unit 101, to the server 1 by means of the data transmitting/receiving function with respect to the server 1.

[Preprocessing Device]

Figure 3:
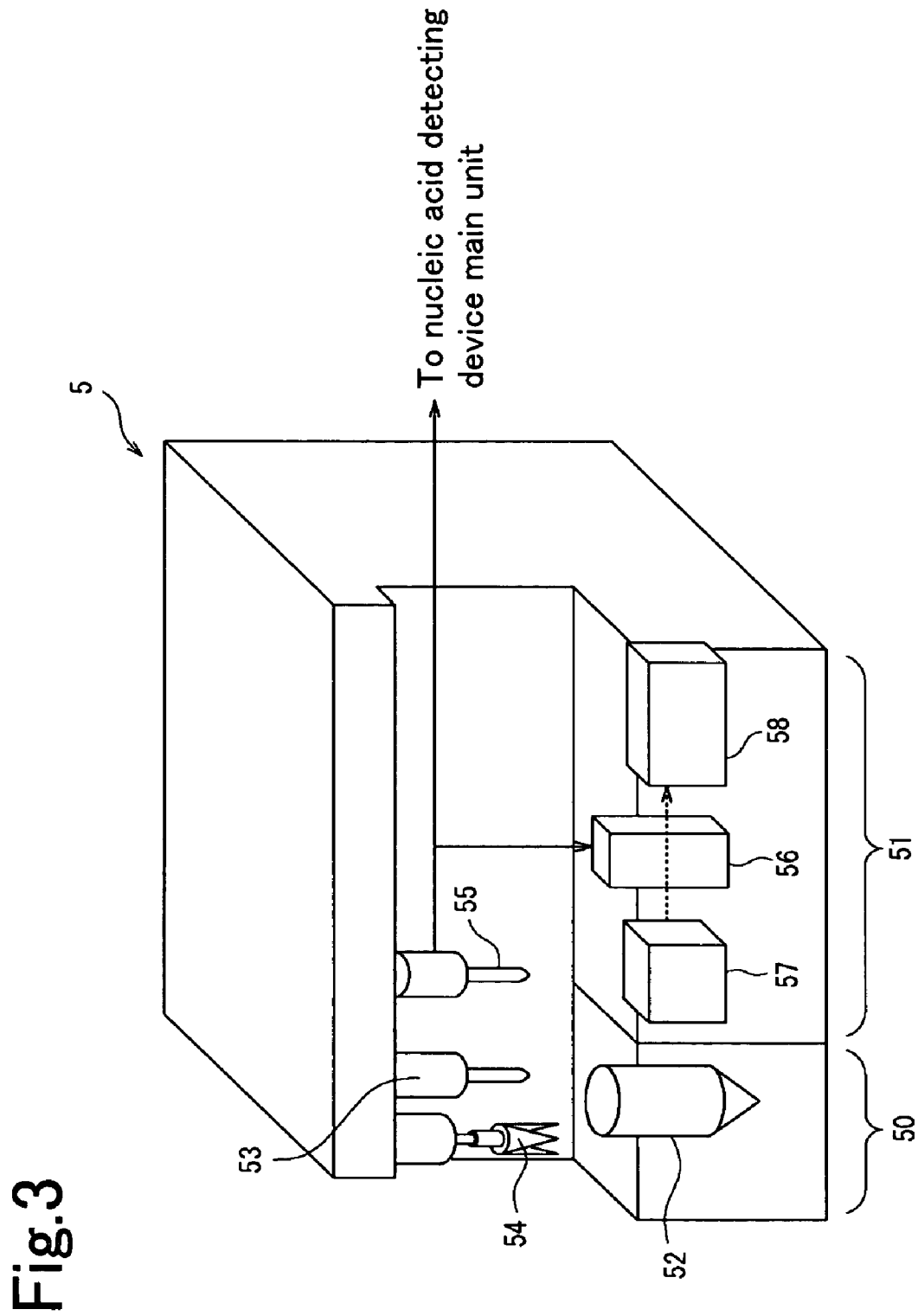
FIG. 3 is a schematic structure view of a preprocessing device.

As shown in FIG. 3, the preprocessing device main unit 5 mainly has a preprocessing unit 50 that conducts a preprocessing to an analyte to prepare a measuring analyte, and a measuring unit 51 that measures the measuring analyte having subjected to the preprocessing.

The preprocessing unit 50 includes an analyte placement part 52 in which a container containing an analyte is placed, a reagent adding part (reagent dispensing pipette) 53 for adding a preprocessing reagent to the container containing an analyte placed in the analyte placement part 52, a blender (homogenizing part) 54 for homogenizing an analyte, a pipette (dispensing part) 55 for dispensing a homogenized (preprocessed) measuring analyte, and a transferring part (omitted in the drawing) for transferring the pipette 55 to the measuring unit 51 or the nucleic acid detecting device main unit 101.

Upon reception of a measurement start instructing signal from the data processing device 6, the preprocessing device adds a preprocessing reagent to the analyte in the analyte placement part 52 (preprocessing reagent adding process), and the analyte is homogenized by the blender 54 (homogenizing process) to prepare a measuring analyte.

Then the measuring analyte (hereinafter, simply referred to as "sample") is suctioned with the pipette 55, and the pipette 55 moves to the nucleic acid detecting device main unit 101 in the case of usual nucleic acid detection where the sample is injected into a sample container 22 placed in the nucleic acid detecting device main unit 101.

On the other hand, in the case of quality control, the pipette 55 having suctioned a quality control analyte for measurement that is prepared from the quality control analyte for preprocessing by a preprocessing moves to an absorbance measuring cell 56 where the quality control analyte for measurement is injected into the absorbance measuring cell 56 of the measuring unit 51.

The absorbance measuring cell 56 is irradiated with light from an optical source 57, and the light is detected by a detector (light-receiving part) 58, and an absorbance of the sample having subjected to a preprocessing is measured. The measured absorbance (measurement data) is transmitted to the data processing device 6 by a transmitting unit (omitted in the drawing) of the preprocessing device main unit 5.

It is to be noted that the preprocessing is not limited to homogenization but may be extraction of nucleic acid and the like.

[Nucleic Acid Detecting Device]

Figure 4:
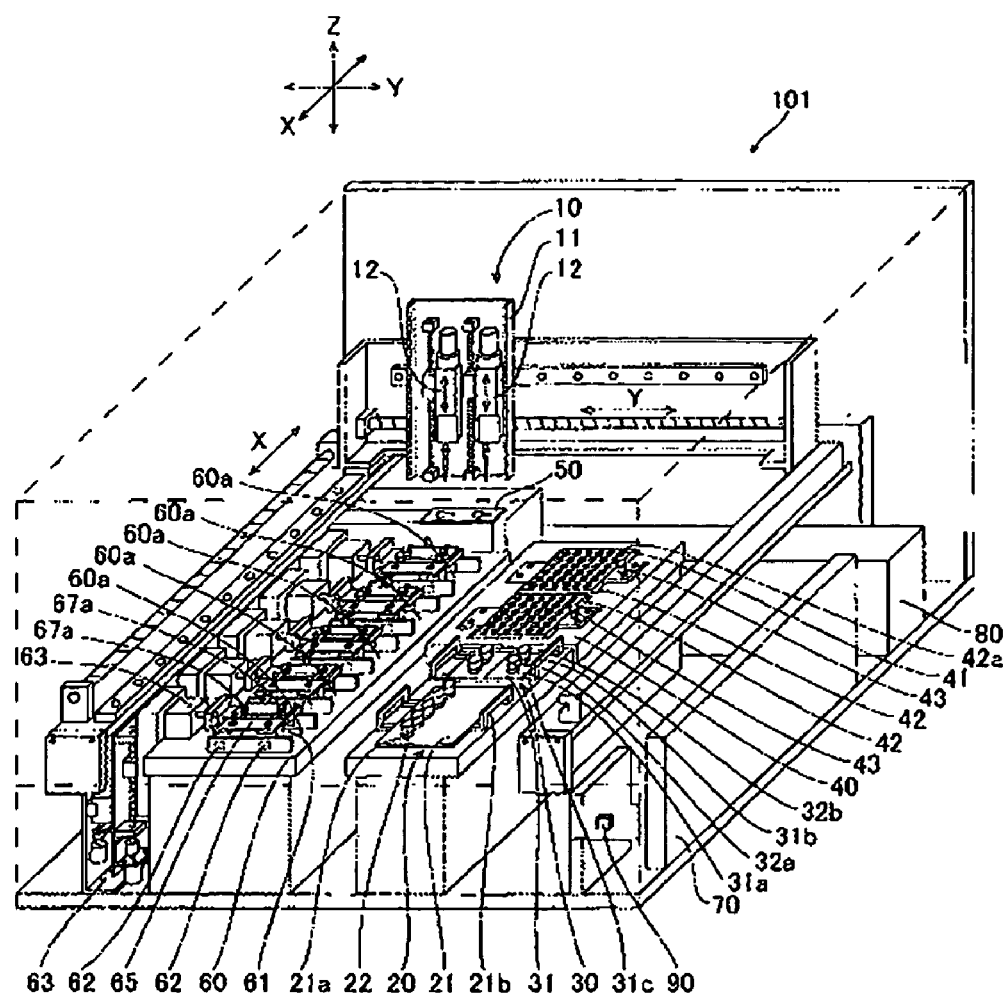
FIG. 4 is a perspective view of a nucleic acid detecting device.
Figure 5:
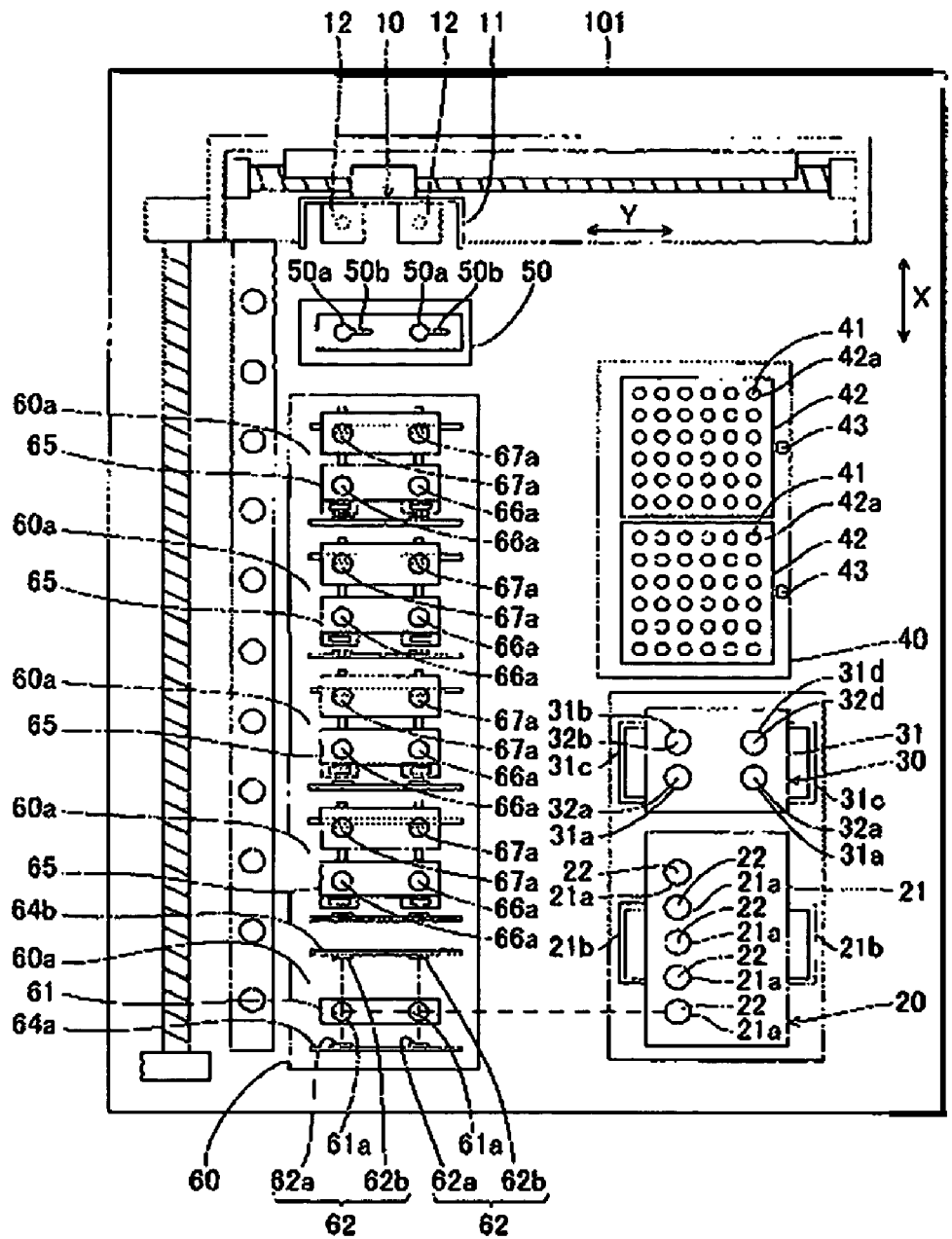
FIG. 5 is a plan view of a nucleic acid detecting device.

The nucleic acid detecting device main unit 101 is made up in the manners as illustrated in FIGS. 4 and 5, and the details of this device are described in U.S. Pre-Grant Publication No. 2005-42138. Here, structure and operation of the nucleic acid detecting device main unit 101 will be briefly explained.

First, the pipette having moved from the preprocessing device main unit 5 injects a preprocessed sample into the sample container 22 placed in a sample container placing hole 21*a* of a sample container base 21.

In a primer reagent container placing hole 31*a* and an enzyme reagent container placing hole 31*b* on the front left side of a reagent container placing part 30, a primer reagent container 32*a* containing a primer reagent for CK19 (cytokeratin 19) and an enzyme reagent container 32*b* containing an enzyme reagent are respectively placed. In a primer reagent container placing hole 31*a* on the front right side of the reagent container placing part 30, a primer reagent container 32*a* containing a primer reagent for Arabidopsis (hereinafter, simply referred to as "arabido") which is an internal standard substance is placed. In an arabido container placing hole 31*d* on the front right side, an arabido solution container 32*d* containing a predetermined amount of arabido is placed.

In a recess (not shown) of a chip placing part 40, two racks 42 each accommodating 36 disposable pipette chips 41 are fitted. Also in two detection cell placing holes in a reaction part 61 of each reaction detecting block 60*a*, two cell portions 66*a* of a detection cell 65 are placed.

When operation of the nucleic acid detecting device main unit 101 starts in this condition, first, an arm portion 11 of a dispensing mechanism part 10 moves to the chip placing part 40 from its initial position, and then in the chip placing part 40, two syringe portions 12 of the dispensing mechanism part 10 are moved downward. As a result, tip ends of nozzle portions of the two syringe portions 12 are pressed into upper openings of the two pipette chips 41, so that the pipette chips 41 are automatically attached to the tip ends of the nozzle portions of the two syringe portions 12. Then after the two syringe portions 12 have been moved upward, the arm portion 11 of the dispensing mechanism part 10 is moved in the X-axial direction toward above the two primer reagent containers 32*a* respectively containing primer reagents for CK19 and arabido, placed on the reagent container placing base 31. Then the two syringe portions 12 are moved downward so that the tip ends of the two pipette chips 41 attached to the nozzle portions of the two syringe portions 12 are respectively inserted into the liquid surfaces of the primer reagents for CK19 and arabido in the two primer reagent containers 32*a*. Then the primer reagents for CK19 and arabido in the two primer reagent container 32*a* are suctioned by pumps of the syringe portions 12.

After the two syringe portions 12 have moved upward following suction of the primer reagents, the arm portion 11 of the dispensing mechanism part 10 is moved above a reaction detecting block 60*a* situated in the innermost position from front face (innermost from the front face of the device). In this case, the arm portion 11 of the dispensing mechanism part 10 is moved without passing above other second to fifth reaction detecting blocks 60*a* counted from the innermost one. In the innermost reaction detecting block 60*a*, the two syringe portions 12 are moved downward, so that the two pipette chips 41 attached to the nozzle portions 12*a* of the two syringe portions 12 are respectively inserted into the two cell portions 66*a* of the detection cell 65. Then two primer reagents for CK19 and arabido are respectively discharged into two cell portions 66*a* by means of pumps of the syringe portions 12 (primer reagent dispensing process).

Then the pipette chips 41 are disposed, and after two new pipette chips 41 are automatically attached to the tip ends of the nozzle portions of the two syringe portions 12, an enzyme reagent within the enzyme reagent container 32*b* is discharged into two cell portions 66*a* of the detection cell 65 in a similar manner as described above (enzyme reagent dispensing process).

Then, also in a similar manner, the arabido solution within the arabido solution container 32*d* is discharged into two cell portions 66*a* of the detection cell 65.

Then, also in a similar manner, the sample (measuring analyte) in the sample container 22 is discharged into two cell portions 66*a* of the detection cell 65 (sample dispensing process).

As a result, a sample for detection of CK19 is prepared in one of the cell portions 66*a* of the detection cell 65 and a sample for detection of arabido is prepared in the other of the cell portions 66*a*.

After completion of discharges of the primer reagents, enzyme reagent, arabido solution and sample into the cell portions, a lid of the detection cell 65 is closed.

After closing the lid, the liquid temperature in the detection cell 65 is raised from about 20° C. to about 65° C. by means of a Peltier module of the reaction part 61 for amplifying a target gene (CK19) and arabido by the LAMP method.

Then the white turbidity due to magnesium pyrophosphate generated with amplification is detected by turbidimetry. Concretely, a light beam having a diameter of about 1 mm is emitted from a LED optical source 62*a* of the turbidity detecting part 62 to the cell portion 66*a* of the detection cell 65 (measurement data acquiring part) in amplification reaction via a light emitting groove of the reaction part 61. Then the emitted light is received by a photodiode light receiving part 62*b*.

In this manner, the liquid turbidity in the cell portion 66*a* of the detection cell 65 in amplification reaction is detected (monitored) in real time (detection process).

Measurement data of CK19 and measurement data of arabido measured at the photodiode light receiving part 62*b* (measurement data acquiring means) are transmitted to data processing device 6 by the transmitter (not shown) possessed by the nucleic acid detecting device main unit 101.

Figure 6:
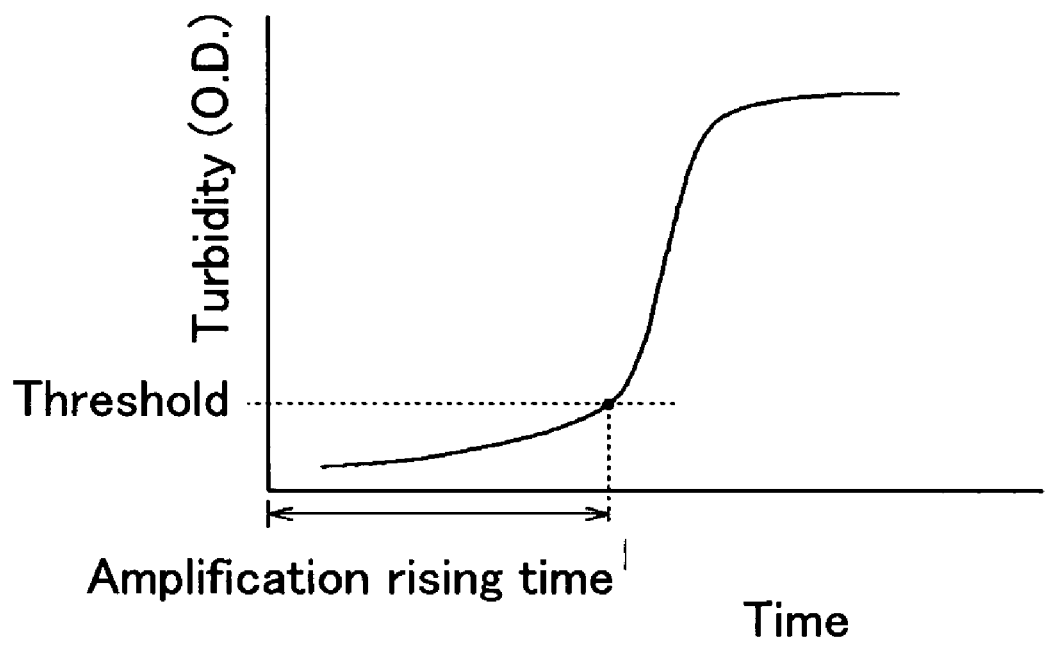
FIG. 6 is a graph showing relationship between amplification raising time and concentration.

As a result, in the data processing device 6, when the horizontal axis represents time, and the vertical axis represents turbidity (O.D.: Optical Density), measurement data of CK19 as shown in FIG. 6 is obtained. From this measurement data of CK19, amplification rising time which is a time required for the target gene (CK19) in the sample to rapidly increase the copy numbers is detected by comparing the turbidity with a predetermined threshold.

On the other hand, the data processing device 6 also creates measurement data of arabido in which the horizontal axis represents time and the vertical axis represents turbidity, from the measurement data of arabido in the same manner as described above, and acquires amplification rising time of arabido based on the measurement data. Based on the amplification rising time of arabido, the data processing device 6 corrects the amplification rising time of CK19. This correction prevents amplification inhibiting substances in the sample from influencing on the measurement result.

Figure 7:
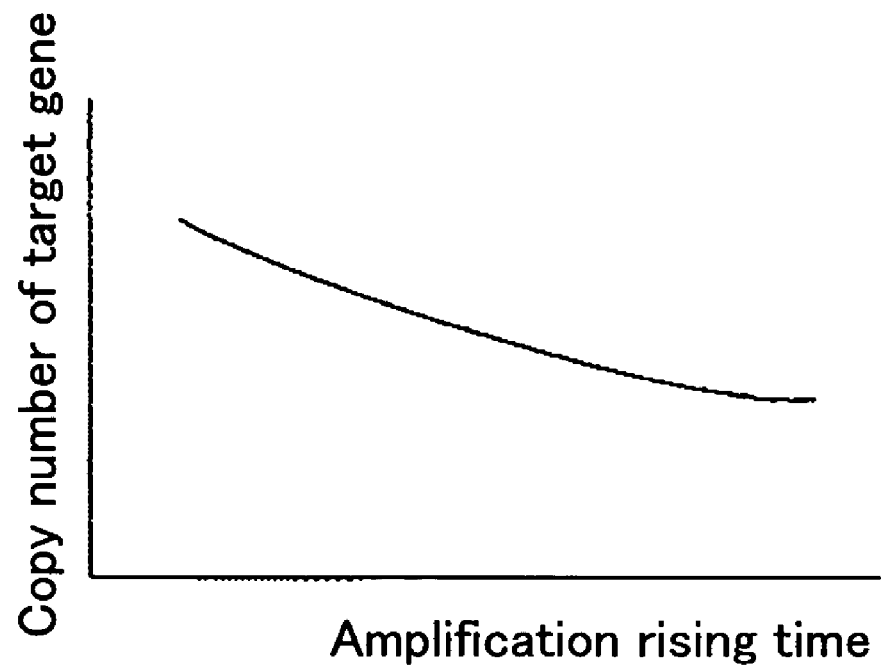
FIG. 7 is a graph describing a calibration curve showing relationship between amplification rising time and copy number of target gene.

Then, based on the calibration curve prepared in advance from the measurement result of calibrator of CK19, as shown in FIG. 7, quantity (copy number) of the target gene (CK19) is calculated from the corrected amplification rising time of CK19. The calibration curve shown in FIG. 7 is a curve in which the horizontal axis represents amplification rising time and the vertical axis represents copy number (copy number/µL) of target gene (CK19), and in general, the shorter the amplification rising time, the higher the concentration of the target gene is.

The calculated quantitative data (measurement data) of target gene is screen-displayed by a display unit of the data processing device 6 or by other display unit. The data processing device 6 determines a qualitative determination result for supporting diagnosis, from the quantitative measurement data (amplification rising time, copy number), and screen-displays it by a display unit of the data processing device or by other display unit.

Determination is made in the following manner. For example, when the number of copies is 250 or less as shown in FIG. 8, or when the turbidity fails to reach a threshold even after a predetermined time has lapsed in the measurement data shown in FIG. 6, it is determined as "ND", and when the number of copies falls within the range of 250 to $5 \times 10^3$, it is determined as "+", and when the number of copies is larger than $5 \times 10^3$, it is determined as "++". Here, qualitative degree of cancer metastasis is represented by "ND: no metastasis is detected", "+: little metastasis is detected", and "++: metastasis is detected". The system 2 determines and displays a qualitative result that is useful for supporting definite diagnosis, from the quantitative measurement data (quantity of cells derived from cancer), which allows a physician to rapidly make diagnosis during a surgery and determines a region of dissection.

[External Quality Control Computer; Server]

Figure 9:
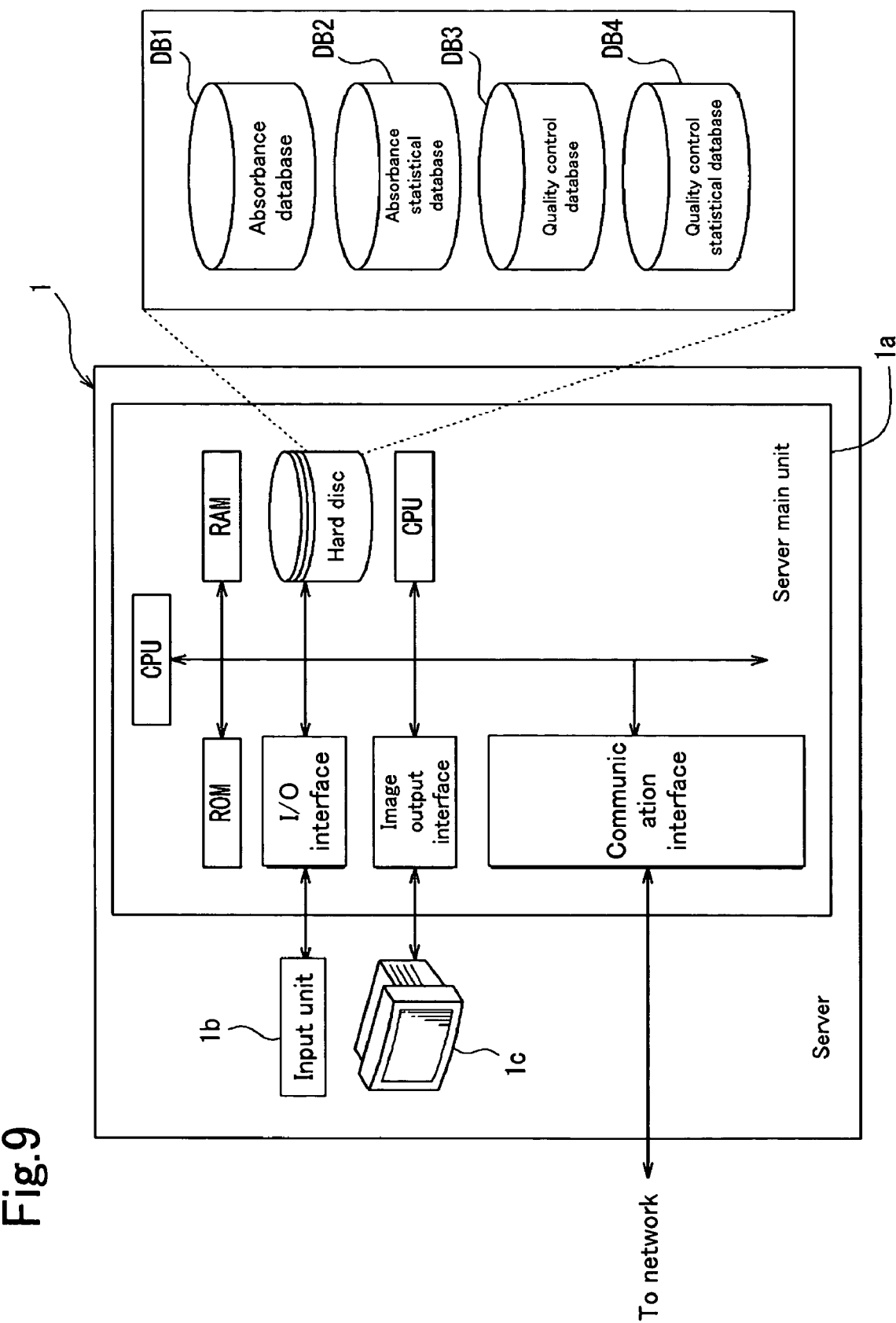
FIG. 9 is a configuration view of an external quality control computer (server).

As shown in FIG. 9, the server 1 serving as an external quality control computer has a server main unit 1a, an input unit 1b such as keyboard and mouse, and a display unit 1c such as display. The server main unit 1a has CPU serving as a processor, a ROM, a RAM, an I/O (input/output) interface, an image output interface, a communication interface and a hard disc.

The hard disc stores absorbance database DB1, absorbance statistical database DB2, quality control database DB3, and quality control statistical database DB4, and these databases will be described later.

[External Quality Control of Preprocessing]

In the case of external quality control of the preprocessing device 5, an analyte for quality control (quality control analyte for preprocessing) is preprocessed by the preprocessing device main unit 5 to prepare a quality control analyte for measurement, and absorbance of the quality control analyte for measurement is measured.

The quality control analyte for preprocessing is constructed as a pseudo tissue including a known amount of target nucleic acid or a cell containing a known amount of target nucleic acid, and a holder capable of holding the target nucleic acid or the cell containing target nucleic acid.

The pseudo tissue is so constructed that when absorbance is measured after a predetermined preprocessing by the preprocessing device main unit 5, a predetermined reference value (display value) is obtained.

As a nucleic acid used in such a pseudo tissue, not only DNA and RNA, but also PNA, BNA and their related artificial nucleic acids may be used.

As a cell used in such as a pseudo tissue, any cells containing a target nucleic acid can be employed without particular limitations.

As a holder, those being in a solid state at room temperature and fluidize due to destruction of the solid state when heated to a certain temperature are preferably used. Also those having solidity comparable to that of biological tissue in their solid states are preferred.

Preferably, the holder includes a gelling agent. A gelling agent is a substance that makes a solution gelate when it is added to a solvent. Examples of the gelling agent include natural polymers such as agar, agarose, carrageenan, alginic acid, alginate, pectin, collagen, gelatin and gluten, and synthetic polymers such as polyvinyl alcohol (PVA), polyethylene glycol (PEG) and polyacrylamide (PAA). In the pseudo tissue according to the present embodiment, one or more selected from the above synthetic polymers and natural polymers may be used. Examples of a solvent to which a gelling agent is added include, but are not limited to, water, TE (Tris EDTA), TAE (Tris-Acetate EDTA) and TBE (Tris-Borate EDTA).

Figure 10:
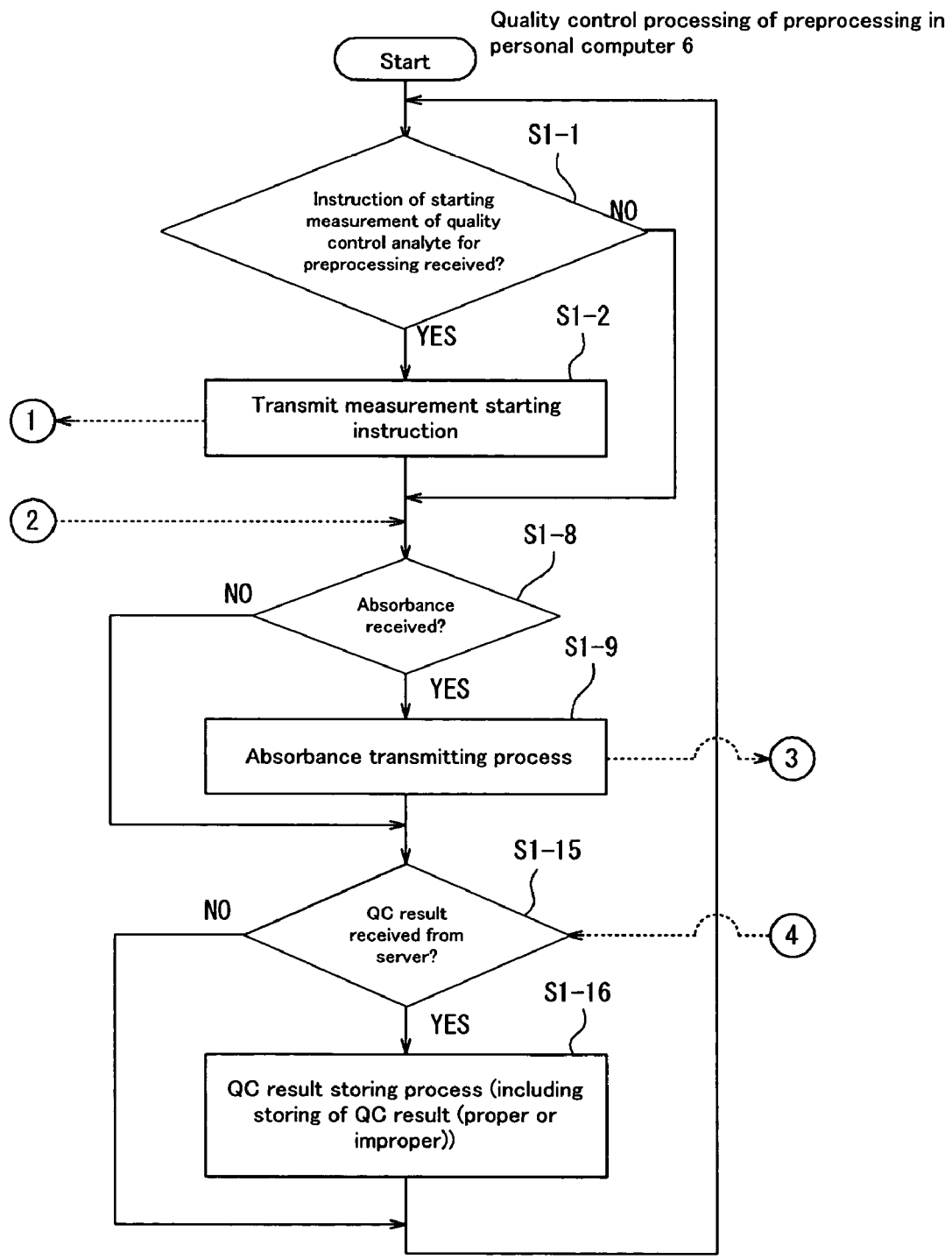
FIG. 10 is a flow chart showing a quality control processing of preprocessing in a personal computer 6.
Figure 11:
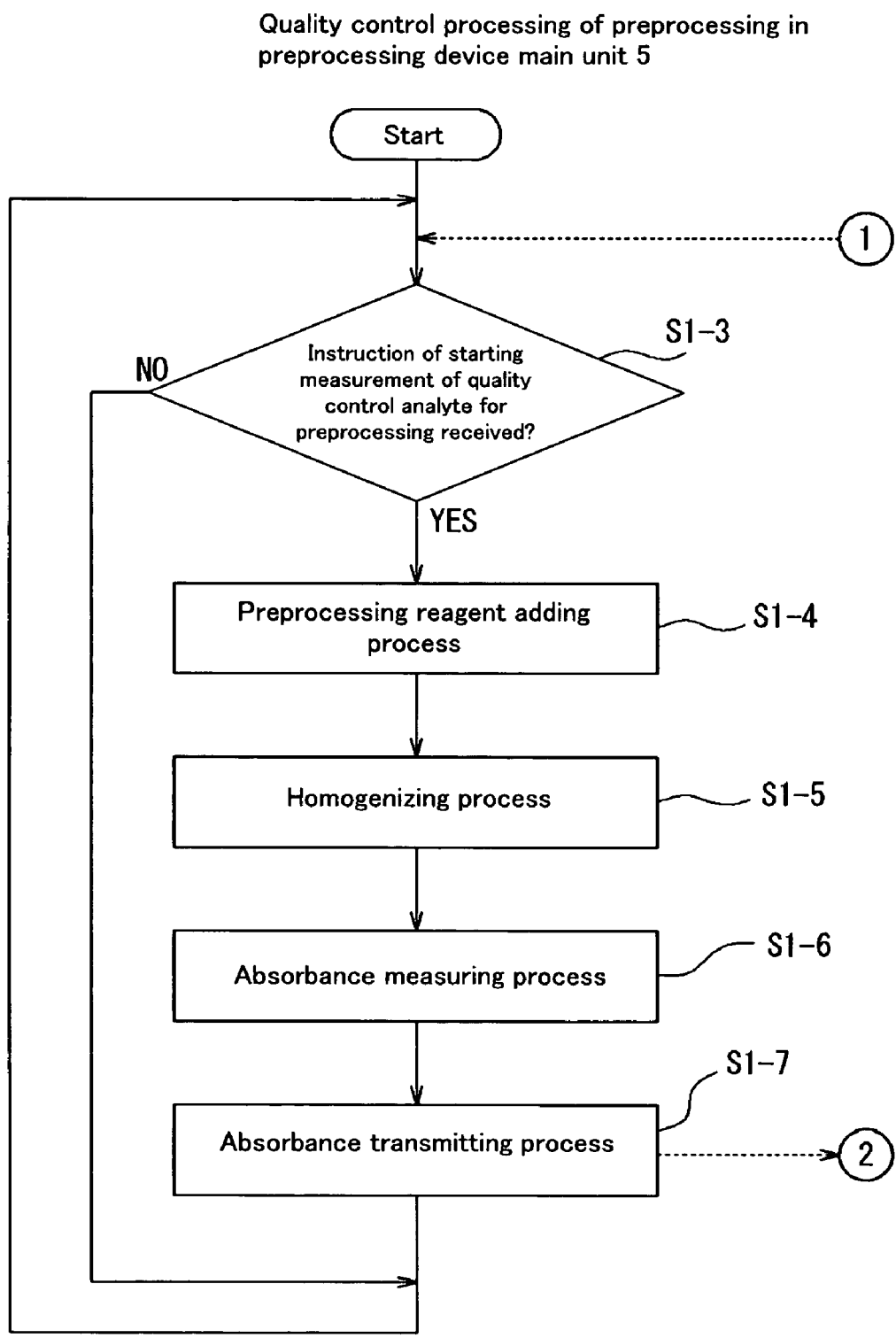
FIG. 11 is a flowchart showing a quality control processing of preprocessing in a preprocessing device main unit 5.
Figure 12:
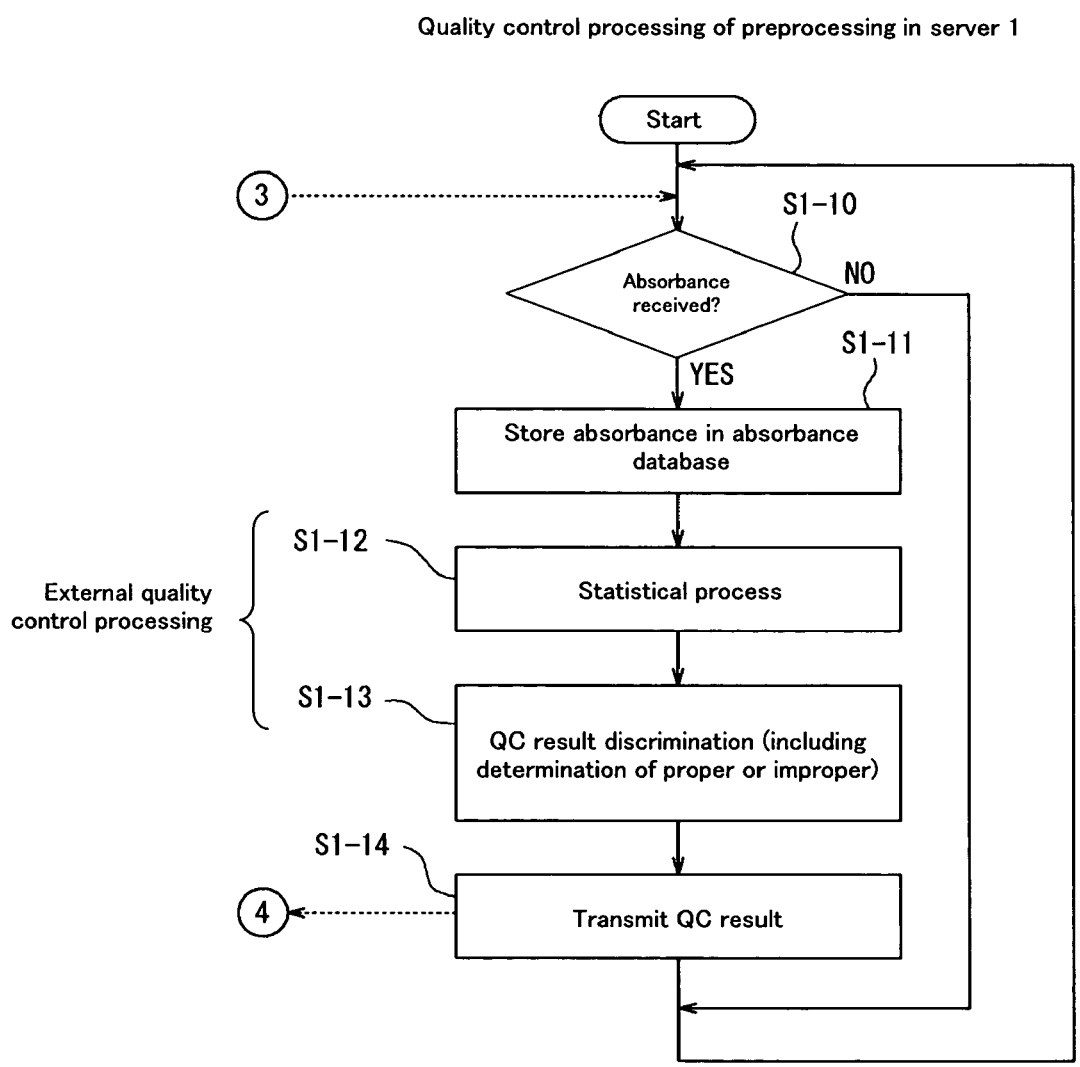
FIG. 12 is a flowchart showing a quality control processing of preprocessing in a server 1.

FIGS. 10 to 12 show processings of the personal computer 6, the preprocessing device main unit 5, and the server 1 for quality control of preprocessing.

The external quality control processing is executed once or several times a day, and a normal measurement of analyte is executed after executing an external quality control processing. First, in the case of quality control, the pseudo tissue (quality control analyte for preprocessing) is placed in the analyte placement part 52 of the preprocessing device main unit 5.

Then a user (e.g., staff in hospital) inputs a start instruction via the input unit such as keyboard and mouse of the personal computer 6 in the system 2 so as to start the external quality control of the preprocessing device main unit 5, and upon reception of the instruction (Step S1-1: see FIG. 10), the personal computer (control unit) 6 transmits a measurement starting instruction for preprocessing to the preprocessing device main unit 5 (Step S1-2).

Upon response of a signal instructing start of measurement (Step S1-3: see FIG. 11), the preprocessing device main unit 5 causes the preprocessing unit 50 to conduct a preprocessing reagent adding process (Step S1-4) and a homogenizing process (Step S1-5) on a quality control analyte for preprocessing, thereby preparing a quality control analyte for measurement.

The quality control analyte for measurement is supplied to the measuring unit 51 of the preprocessing device main unit 5 where absorbance is measured (Step S1-6). Then the preprocessing device main unit 5 transmits measurement data of the measured absorbance to the personal computer 6 (Step S1-7).

Receiving measurement data of absorbance (Step S1-8: FIG. 10), the personal computer 6 transmits the measurement data to the server 1 (Step S1-9).

Receiving measurement data of absorbance via a network (Step S1-10: see FIG. 12), the server 1 stores the measurement data of absorbance in the absorbance database DB1 (Step S1-11).

The server 1 also executes a statistical process on plural measurement data of absorbance transmitted from preprocessing device main units 5 of a plurality of nucleic acid detecting systems 2 installed in different facilities. Concretely, based on the measurement data of absorbance respectively transmitted from the systems 2 (preprocessing devices) installed in a plurality of facilities, daily average and standard deviation 1SD (Step S1-12) are determined.

The server 1 also determines 2SD which is twice the standard deviation 1SD and 3SD which is three times the standard deviation 1SD. These daily averages of absorbance measurement data of 1SD, 2SD, 3SD are stored in the absorbance statistical database DB2 of the server 1. The absorbance statistical database DB2 also stores measurement data of absorbance obtained by measuring the pseudo tissue preprocessed in the reference system 2a.

FIG. 13 shows contents of the measurement data of absorbance transmitted to the server 1 from the personal computer 6, and the measurement data includes an ID (device ID) of the nucleic acid detecting system 2 by which the absorbance is measured, a lot number of pseudo tissue (quality control analyte for preprocessing), a measured absorbance of pseudo tissue and a measuring time.

FIG. 14 shows measurement data of absorbance stored in the absorbance database DB1 of the server 1, and the measurement data of absorbance shown in FIG. 13 is stored individually by measurement date and time for the systems 2 of different device IDs.

FIG. 15 shows contents of the absorbance statistical database DB2 in the server 1, in which daily averages of absorbance measurement data, 1SD, 2SD, 3SD, as well as measurement data of absorbance measured for pseudo tissue which is preprocessed in the reference system 2a are stored.

Further, upon reception of the measurement data of absorbance, the server 1 determines whether the preprocessing by the preprocessing device is properly executed based on the average calculated in Step S1-12 and 1SD, 2SD or 3SD (Step S1-13).

More specifically, the server 1 determines whether the preprocessing is proper based on the average of measurement data of absorbance and standard deviation 1SD, 2SD or 3SD received within a past preset time (for example, past 24 hours).

Each of 1SD, 2SD and 3SD is a potential reference value for determining whether the received measurement data of absorbance is proper or not, and decision of which one of 1SD, 2SD and 3SD is to be selected rests with a particular facility, and the selected reference value is used for determination.

The process of Step S1-12 and the process of Step S1-13 are called an external quality control processing. The process of Step S1-13 may be omitted. In such a case, the processing may be executed by the personal computer 6 or by the user watching the screen of external quality control result displayed in the personal computer 6.

Determination (QC (Quality Control) result determination) may be made as "proper" if the received measurement data of absorbance falls within the range of 0.227±0.006 and "improper" if it does not fall within the range of 0.227±0.006, assuming that 2SD is selected as a reference value, an average of measurement data of absorbance received in a past preset time is 0.227, and standard deviation (×2)2SD is 0.006, for example. When 1SD is selected as a reference value, the reference value is stricter, and when 3SD is selected as a reference value, the reference value is laxer.

The statistical processing result and the determination result (QC results) by the server 1 is transmitted to the personal computer 6 of the system 2 from which the measurement data of absorbance is transmitted (Step S1-14).

Upon reception of the data of QC result (statistical processing result and the determination result) (Step S1-15), the personal computer 6 executes a process of storing the QC results in a storing means such as hard disc (Step S1-16).

Through the processing described above, the nucleic acid detecting system 2 is provided with information about whether the preprocessing is proper or not.

[External Quality Control of Nucleic Acid Detecting Process]

When external quality control of the nucleic acid detecting device 101 is conducted, a quality control analyte for nucleic acid detection (hereinafter, referred to as simply "control solution") instead of the normal measuring analyte is measured by means of the nucleic acid detecting device main unit 101.

As the control solution, two controls are used: CK19 control (first quality control substance for nucleic acid detection) containing a known amount of CK19 which is a target nucleic acid and lacking arabido which is an internal standard nucleic acid (nucleic acid derived from plant; absent in human body) and Internal control (arabido control; second quality control substance for nucleic acid detection) containing a known amount of arabido which is an internal standard nucleic acid and lacking CK19 which is a target nucleic acid.

First, prior to an external quality control processing (control solution measuring process), a sample container 22 containing CK19 control, and a sample container 22 containing arabido control are placed in the sample container base 21 of the nucleic acid detecting device main unit 101.

Figure 16:
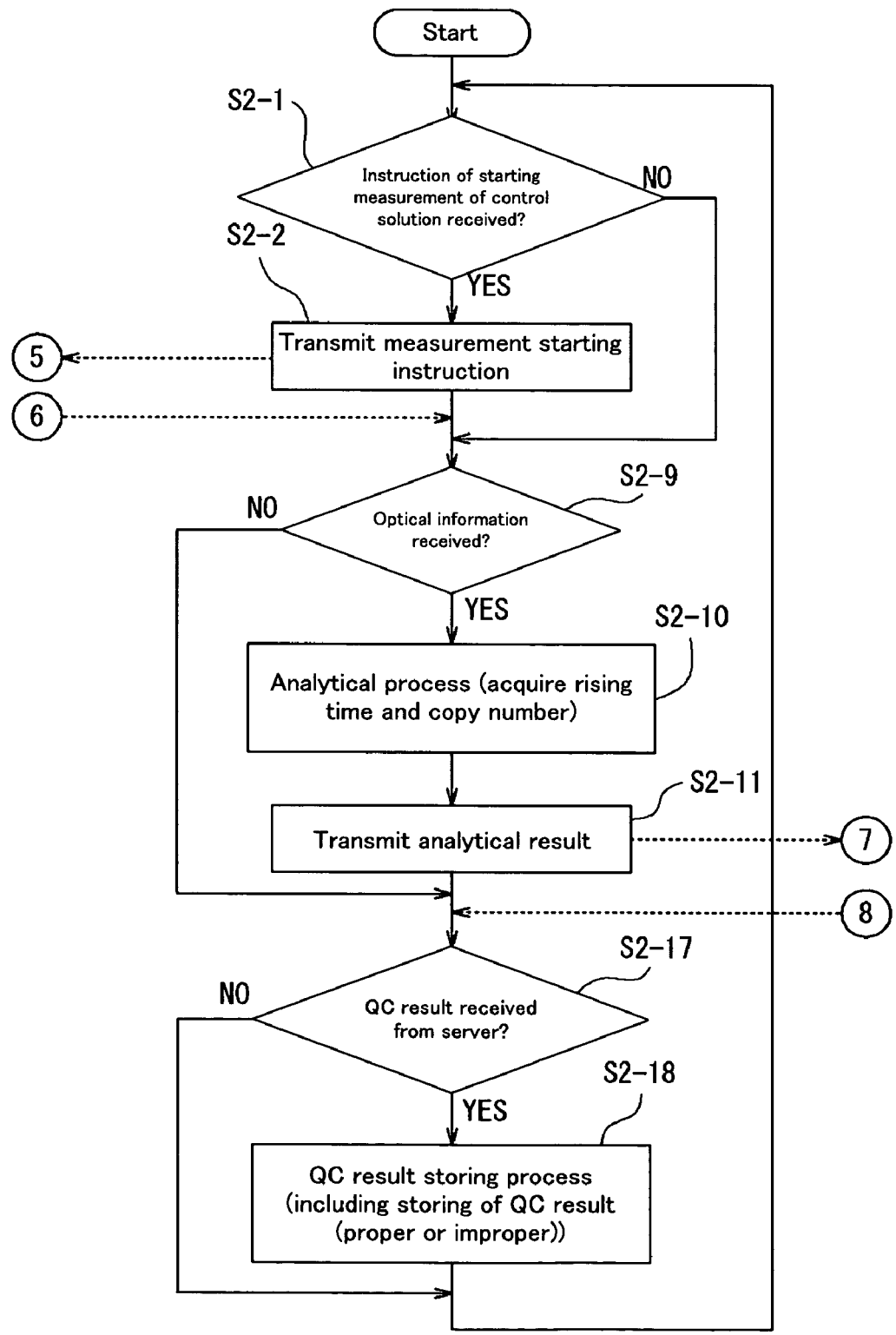
FIG. 16 is a flowchart showing a quality control processing of nucleic acid detecting process in the personal computer 6.

Then a user (e.g., staff of hospital) inputs a start instruction via the input unit such as keyboard and mouse of the personal computer 6 in the system 2 so as to start the external quality control of the nucleic acid detecting device main unit 101, and upon reception of the instruction (Step S2-1: see FIG. 16), the personal computer (control unit) 6 transmits a measurement starting instruction to the nucleic acid detecting device 101 (Step S2-2).

Figure 17:
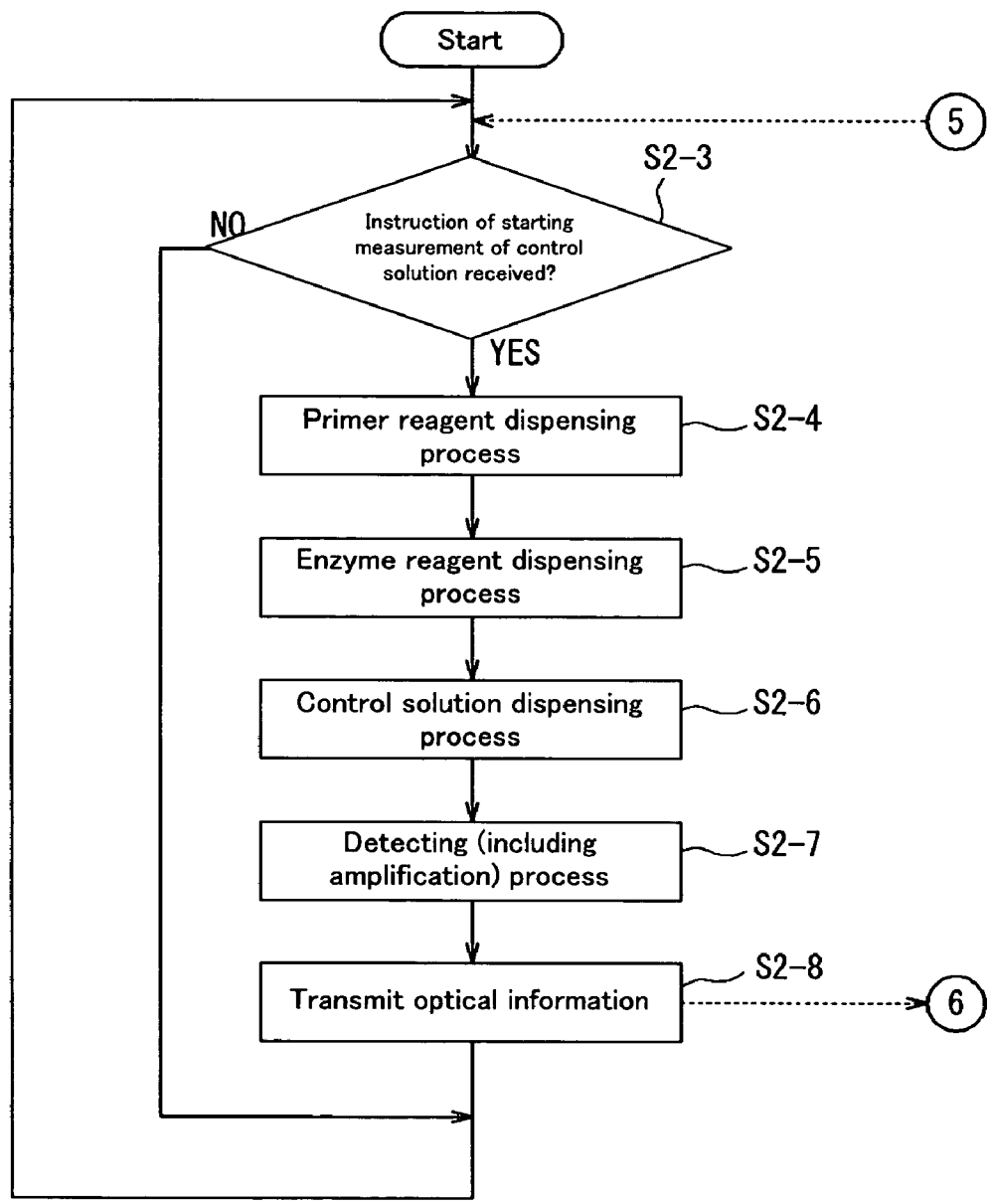
FIG. 17 is a flowchart showing a quality control processing of nucleic acid detecting process in a nucleic acid detecting device main unit 101.

Upon reception of a signal instructing start of measurement (Step S2-3: see FIG. 17), the nucleic acid detecting device main unit 101 conducts a primer reagent dispensing process (Step S2-4), an enzyme reagent dispensing process (Step S2-5), and a control solution dispensing process (Step S2-6) which dispenses the CK19 control solution in the sample container 22 into one of the cell portions 66a of the detection cell 65, and the arabido control solution into the other of the cell portions 66a.

Thereafter, the nucleic acid detecting device main unit 101 amplifies the target nucleic acid (CK19) and arabido according to the LAMP method by warming the liquid temperature in the detection cell 65 from about 20° C. to about 65° C., and conducts a detection process by which the liquid turbidity in each cell portion 66a of the detection cell 65 in the amplification reaction is detected (monitored) in real time by the turbidity detecting part 62 (Step S2-7).

Then the nucleic acid detecting device main unit 101 transmits the detected optical information (measurement data of CK19 and measurement data of arabido) to the personal computer 6 (Step S2-8).

Upon reception of the optical information (liquid turbidity) from the nucleic acid detecting device main unit 101 (Step S2-9: see FIG. 16), the personal computer 6 executes an analytical process for the optical information (Step S2-10). In the analytical process, amplification rising time of CK19, copy number of CK19, and amplification rising time of arabido are calculated.

Amplification rising times of CK19 and arabido are calculated as times required for the liquid turbidity obtained as optical information to exceed a predetermined value, and copy number of CK19 is calculated from the amplification rising time of CK19 based on the calibration curve prepared in advance from a measurement result of a calibrator. In measurement of the control solution, however, correction of amplification rising time of CK19 based on amplification rising time of arabido as described above is not conducted.

The above analytical process is executed for each of the two control substances.

That is, in the analytical process, rising time of CK19 (target nucleic acid) when CK19 control is measured (first measurement data), rising time of arabido (internal standard nucleic acid) when arabido control is measured (second measurement data), rising time of arabido (internal standard nucleic acid) when CK19 control is measured (third measurement data), and rising time of CK19 when arabido control is measured (fourth measurement data) are calculated, and the copy number of CK19 is calculated based on the first measurement data.

The analytical result (measurement data) is transmitted from the personal computer 6 to the server 1 (Step S2-11). FIGS. 19A and 19B show contents of the measurement data transmitted to the server 1. FIG. 19A shows measurement data about CK19 control and FIG. 19B shows measurement data about Internal control.

These measurement data contain a system ID (device ID) by which the control substance is measured, a lot number of control substance, measuring time and the like, as well as the above analytical result. "ND" contained in these measurement data represents that the turbidity does not reach a predetermined value after lapse of predetermined time, namely, a rising time is not detected. The measurement data shown in FIG. 19A is one example, and the measurement data may contain at least the value calculated in Step S2-10.

As can been seen from FIGS. 19A and 19B, rising time is observed in rising time of CK19 (target nucleic acid) when CK19 control is measured (first measurement data), and rising time of arabido (internal standard nucleic acid) when arabido control is measured (second measurement data), which reveals that those expected to be amplified are amplified.

On the other hand, in rising time of arabido (internal standard nucleic acid) when CK19 control is measured (third measurement data), and in rising time of CK19 when arabido control is measured (fourth measurement data), the result "ND" (Not Detected) is obtained and rising time is not observed, which shows that those unexpected to be amplified are not amplified, and propriety.

Therefore, by conducting measurement for every four measurement data as described above, more appropriate external quality control is realized and reliability of detection is improved.

Figure 18:
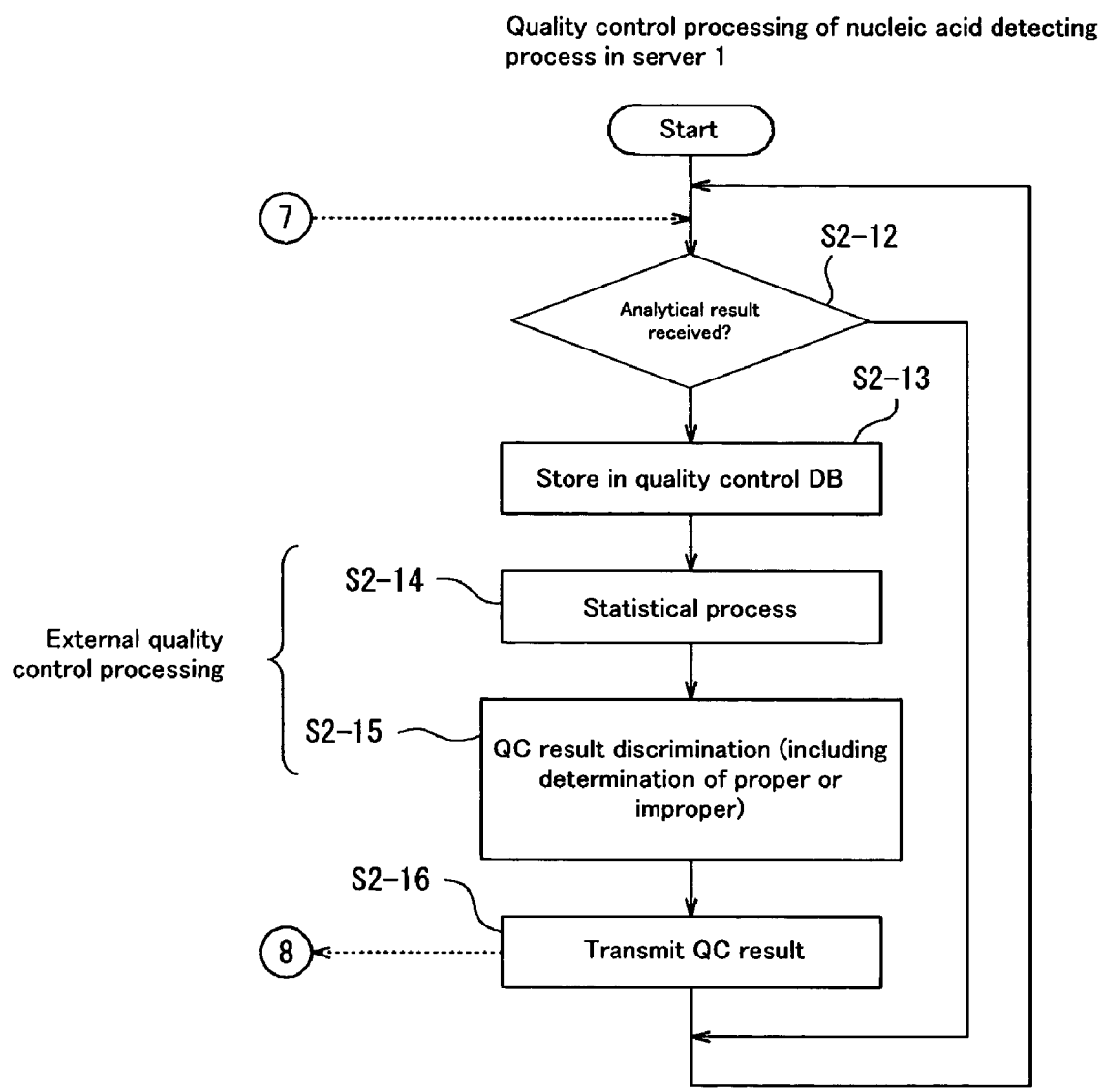
FIG. 18 is a flowchart showing a quality control processing of nucleic acid detecting process in the server 1.

Upon reception of analytical result (measurement data) (Step S2-12: see FIG. 18), the server 1 stores the measurement data in the quality control database DB3 (Step S2-13).

The server 1 also conducts statistical process on plural measurement data transmitted from personal computers 6 of a plurality of nucleic acid test systems 2 installed in different facilities. Concretely, based on the measurement data transmitted from the systems 2 (personal computer 6) installed in the plurality of facilities, daily average and standard deviation 1SD are determined for each measurement item (Step S2-14). The server 1 also determines 2SD which is twice the standard deviation 1SD and 3SD which is three times the standard deviation 1SD. These daily averages of measurement data of 1SD, 2SD, 3SD are stored in the quality control statistical database DB4 of the server 1. The quality control statistical database DB4 also stores measurement data of reference system 2a.

FIGS. 20A and 20B and FIGS. 21A through 21C show contents of the quality control database DB3, in which FIG. 20A shows measurement data of CK19 control and FIG. 20B shows measurement data of Internal control, and lot number of CK19 control, rising time of CK19, copy number of CK19 and rising time of arabido are stored for each measurement date and time, for individual systems 2 having different device IDs.

FIGS. 21A through 21C show measurement data of calibrators C1, C2, C3 as will be described later, and lot number of calibrator, rising time of CK19 and copy number of CK19 are stored for each measurement data and time, for individual systems 2 having different device IDs.

FIGS. 22, 23 and 24 show contents of the quality control statistical database DB4, in which averages, 1SD, 2SD, 3SD, and reference system measurement data are stored for each measurement item (CK19 rising time, copy number of CK19, CK19 rising time) for each measurement object (CK19 control, Internal control, calibrators C1, C2 and C3) for each date.

Further, upon reception of measurement data, the server 1 determines whether the nucleic acid detecting process is properly executed or not (Step S2-15) based on the average, and 1SD, 2SD or 3SD calculated in Step S2-14.

More specifically, the server 1 determines whether the nucleic acid detecting process is properly executed or not based on the average and standard deviation 1SD, 2SD or 3SD of measurement data received in a past preset time (for example, past 24 hours) for every measurement data.

Each of 1SD, 2SD and 3SD is a potential reference value for determining whether the received measurement data is proper or not, and decision of which one of 1SD, 2SD and 3SD is to be used rests with a particular facility, and the selected reference value is used for determination.

Determination (QC (Quality Control) result determination) may be made as "proper" if average of received copy number of CK19 falls within the range of $4.1 \times 10^3 \pm 2.6 \times 10^3$ and "improper" if it does not fall within the range of $4.1 \times 10^3 \pm 2.6 \times 10^3$, assuming that 2SD is selected as a reference value, an average of copy number of CK19 received in a past preset time is $4.1 \times 10^3$, and standard deviation (×2)2SD is $2.6 \times 10^3$, for example. Determinations for rising time of CK19 and rising time of arabido are also conducted in a similar manner.

The process of Step S2-14 and the process of Step S2-15 are called an external quality control processing. The process of Step S2-15 may be omitted. In such a case, the processing may be executed by the personal computer 6 or by the user watching the screen of external quality control result displayed in the personal computer 6.

The statistical process result and the determination result (QC results) produced by the server 1 is transmitted to the personal computer 6 of the system 2 from which the measurement data was transmitted (Step S2-16).

Upon reception of the data of QC result (statistical processing result and the determination result) (Step S2-17, see FIG. 16), the personal computer 6 executes a process of storing the QC results in a storing means such as hard disc (Step S2-18).

Through the above processing, the nucleic acid detecting system 2 is provided with information about whether the nucleic acid detection process is properly executed or not.

[External Quality Control of Calibration Curve Preparing Process]

In external quality control of calibration curve preparing process in the nucleic acid detecting device main unit 101, a calibrator instead of a usual measuring analyte is measured by the nucleic acid detecting device main unit 101.

A calibrator contains a predetermined amount of CK19 which is a target nucleic acid, and three calibrators C1, C2 and C3 containing different amounts of CK19 are used. The calibrator C1 has a copy number of $2.5 \times 10^3$ by indicated value (standard value), the calibrator C2 has a copy number of $2.5 \times 10^5$ by indicated value (standard value), and the calibrator C3 has a copy number of $2.5 \times 10^7$ by indicated value (standard value).

The sample containers 22 containing these calibrators C1, C2, C3 are placed on the sample container base 21 of the nucleic acid detecting device main unit 101 prior to the calibration curve preparing process.

Figure 25:
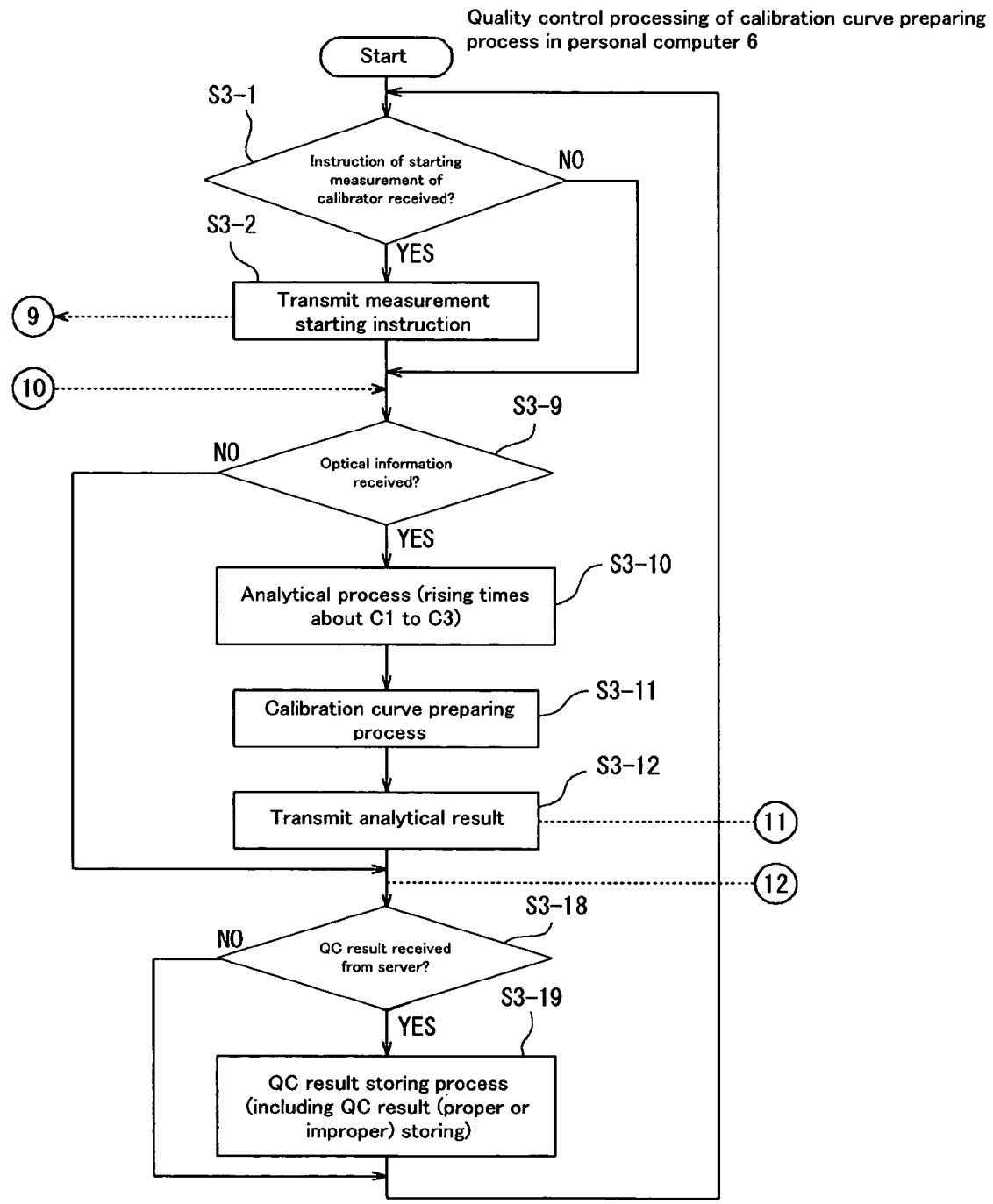
FIG. 25 is a flowchart showing a quality control processing of calibration curve preparing process in the personal computer 6.

Then a user (e.g., staff of hospital) inputs a start instruction via the input unit such as keyboard and mouse of the personal computer 6 in the system 2 so as to start the calibration curve preparing process (calibrator measuring process) of the nucleic acid detecting device main unit 101, and upon reception of the instruction (Step S3-1: see FIG. 25), the personal computer (control unit) 6 transmits an instruction for starting measurement to the nucleic acid detecting device 101.

Figure 26:
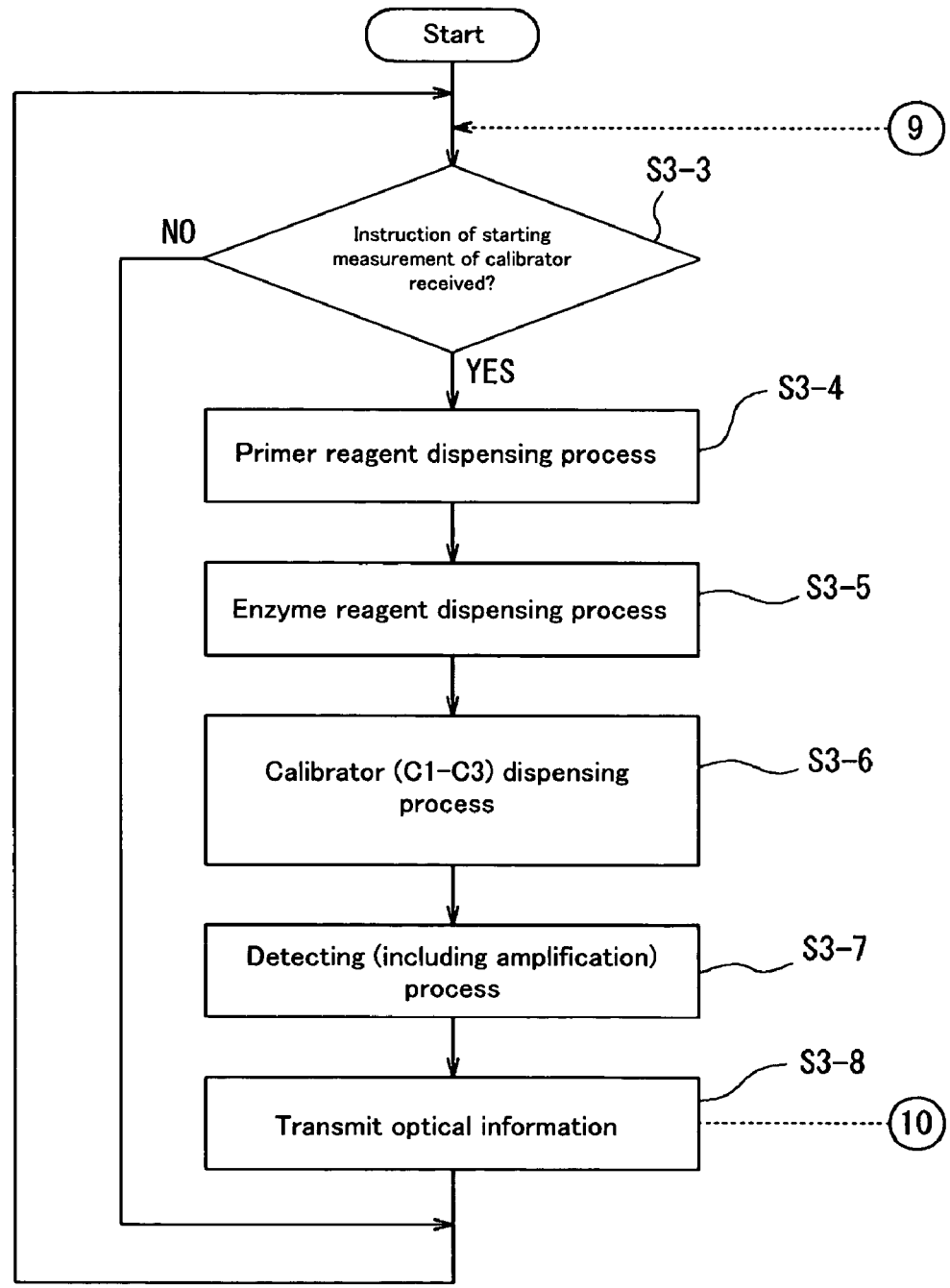
FIG. 26 is a flowchart showing a quality control processing of calibration curve preparing process in the nucleic acid detecting device.

Upon reception of a signal instructing start of measurement (Step S3-3: see FIG. 26), the nucleic acid detecting device main unit 101 conducts a primer reagent dispensing process (Step S3-4), an enzyme reagent dispensing process (Step S3-5), and a calibrator dispensing process (Step S3-6) which dispenses the calibrators in the sample containers 22 into one of the cell portions 66a of the detection cell 65 for each of the calibrators C1 to C3.

Thereafter, the nucleic acid detecting device main unit 101 amplifies the target nucleic acid according to the LAMP (gene amplification) reaction by warming the liquid temperature in the detection cell 65 from about 20° C. to about 65° C., and conducts a detection process by which the liquid turbidity in each cell portion 66a of the detection cell 65 in the amplification reaction is detected by the turbidity detecting part 62 (Step S3-7).

Then the nucleic acid detecting device main unit 101 transmits the detected optical information (measurement data) to the personal computer 6 (Step S3-8).

Upon reception of the optical information (liquid turbidity) of each calibrator C1, C2, C3 from the nucleic acid detecting device main unit 101 (Step S3-9: see FIG. 25), the personal computer 6 conducts an analytical process of the optical information (Step S3-10).

In the analytical process, amplification rising time of each calibrator C1, C2, C3 is calculated. As is already described, amplification rising time is calculated as a time required for the turbidity obtained as optical information to exceed a predetermined value.

Based on the currently holding calibration curve and the copy number of indicated value of each calibrator C1, C2, C3, the personal computer 6 prepares a new calibration curve from the rising time calculated for each calibrator C1, C2, C2 (Step S3-11), and calculates a copy number of CK19 of each calibrator C1, C2, C3 based on the new calibration curve.

The rising time of CK19 and the copy number of CK19 (measurement data) are transmitted to the server 1 from the personal computer 6 (Step S3-12). FIGS. 19C, 19D and 19E show contents of measurement data transmitted to the server 1, in which FIG. 19C shows measurement data about calibrator C1, FIG. 19D is measurement data about calibrator C2, and FIG. 19E is measurement data about calibrator C3.

These measurement data contain system ID (device ID) by which the calibrator is measured, lot number of calibrator, measuring time and the like information, as well as rising time and copy number of CK19.

Figure 27:
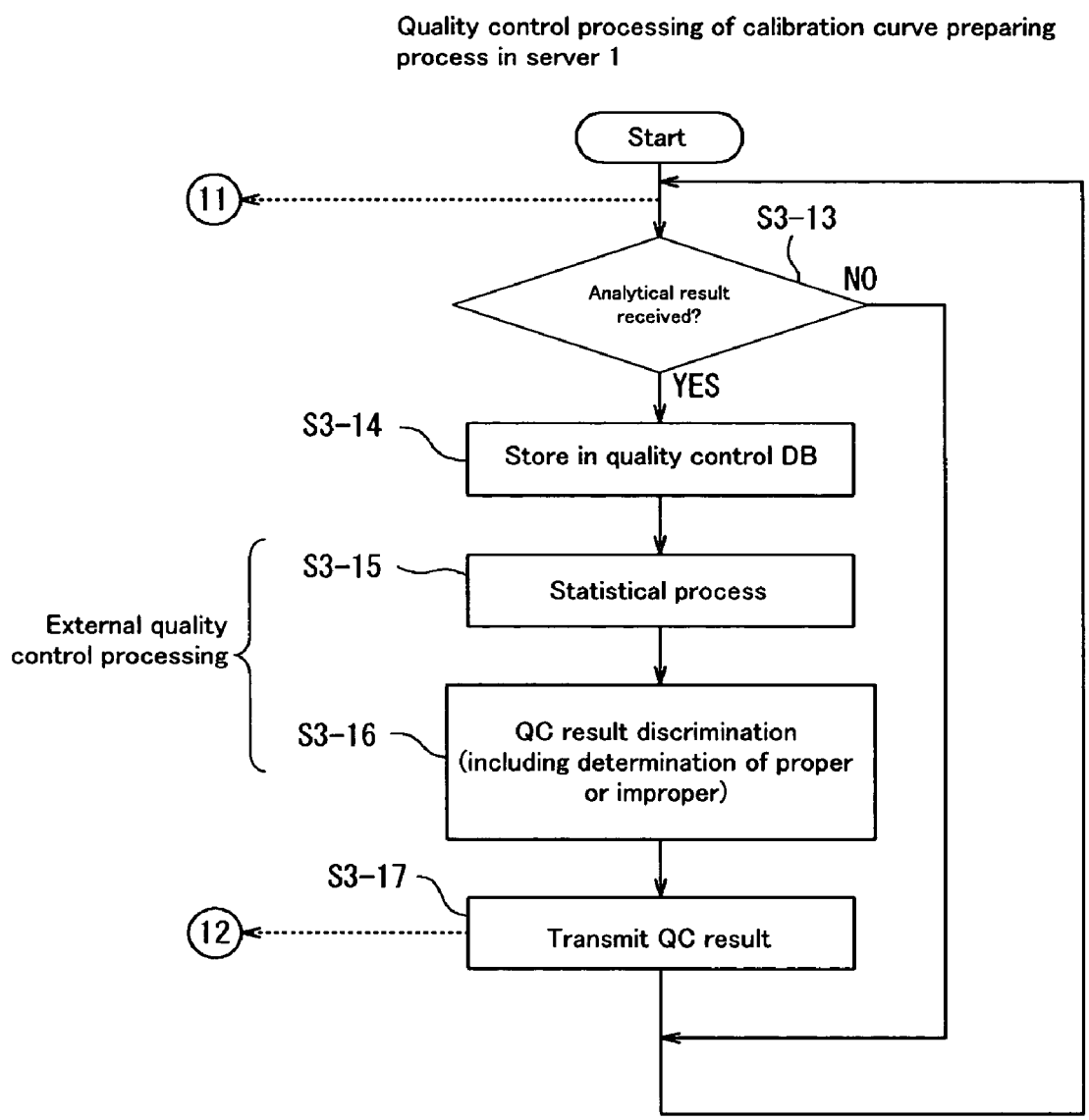
FIG. 27 is a flowchart showing a quality control processing of calibration curve preparing process in the server 1.

Upon reception of the analytical result (measurement data) (Step S3-13: see FIG. 27), the server 1 stores the measurement data in the quality control database DB3 (Step S3-14).

The server 1 also conducts statistical process on plural measurement data transmitted from the nucleic acid detecting devices of a plurality of nucleic acid detecting systems 2 installed in different facilities. Concretely, based on the measurement data transmitted from the systems 2 (personal computer 6) installed in the plurality of facilities, daily average and standard deviation 1SD are determined for each measurement item (Step S3-15). The server 1 also determines 2SD which is twice the standard deviation 1SD and 3SD which is three times the standard deviation 1SD. These daily averages of measurement data of 1SD, 2SD, 3SD are stored in the quality control statistical database DB4 of the server 1. The quality control statistical database DB4 also stores measurement data of reference system 2a.

As is already described, FIGS. 21A through 21C show measurement data of calibrators C1, C2, C3. FIGS. 22, 23 and 24 show contents of quality control statistical database DB4.

Further, upon reception of measurement data, the server 1 determines whether the calibration curve preparing process is properly executed or not based on the average and 1SD, 2SD or 3SD calculated in Step S3-15 (Step S3-16). This determination is similar to the determination for propriety in the nucleic acid detecting process as described above.

The process of Step S3-15 and the process of Step S3-16 are called an external quality control processing. The process of Step S3-16 may be omitted. In such a case, the processing may be executed by the personal computer 6 or by the user watching the QC result screen displayed in the personal computer 6.

The statistical processing result and the determination result (QC results) produced by the server 1 is transmitted to the personal computer 6 of the system 2 from which the measurement data was transmitted (Step S3-17).

Upon reception of the data of QC result (statistical processing result and the determination result) (Step S3-18, see FIG. 25), the personal computer 6 executes a process of storing the QC results in a storing means such as hard disc (Step S3-19).

Through the above processing, the nucleic acid detecting system 2 is provided with information about whether the calibration curve preparing process is properly executed or not.

[Viewing Process of External Quality Control Screen]

Figure 28:
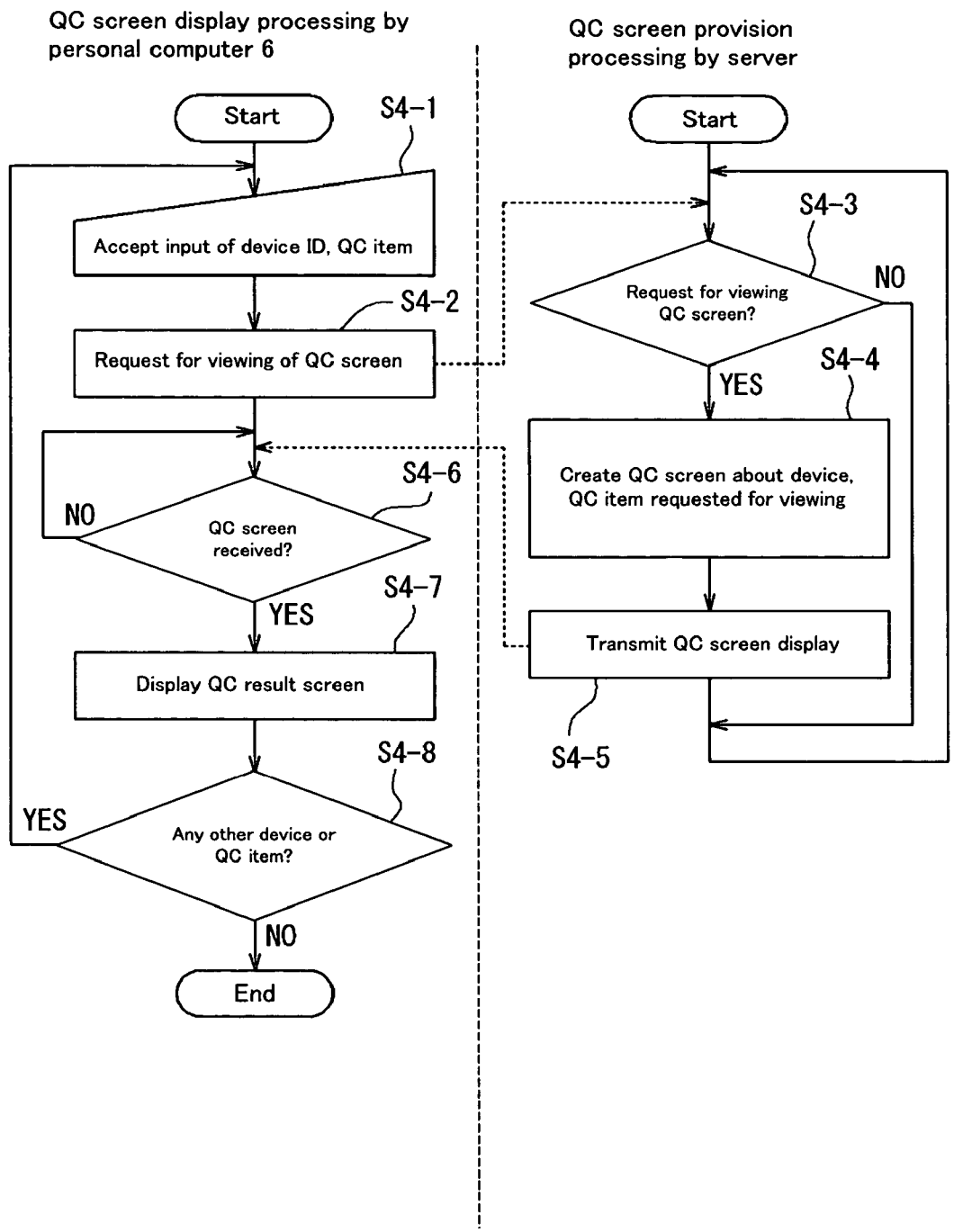
FIG. 28 is a flowchart showing a QC screen viewing process.

FIG. 28 shows a process for displaying an external quality control result screen (QC screen) in the personal computer 6 (which may be a terminal device provided in the facility where the nucleic acid detecting system 2 is installed, or a terminal device provided in other location).

First, a user inputs a device ID in the nucleic acid detecting system 2 which the user wants to display on the QC screen, and an external quality control item (QC item) which the user want to display, on the personal computer 6. Upon reception of these inputs (Step S4-1), the personal computer 6 transmits the device ID and the QC item to the server 1 and requests for viewing of the QC screen (Step S4-2).

Upon reception of the viewing request of the QC screen (Step S4-3), the server 1 prepares a QC screen of the QC item for which the viewing request is made, of the nucleic acid detecting system 2 for which the viewing request is made based on the information stored in the database DB1, DB2, DB3 and DB4 (Step S4-4). Then the server 1 transmits the prepared QC screen to the personal computer 6 from which the viewing request is made (Step S4-5). In this manner, the server 1 enables a QC screen to be viewed from the external via a network.

Upon reception of the QC screen, the personal computer 6 makes a display unit of the personal computer 6 display the QC screen. As a result, the user can view the QC screen and check whether the nucleic acid detecting system 2 is conducting reliable detection at any time.

The processing similar to the above may be repeated (Step S4-8) if the user subsequently wants to view a QC screen about other device or other QC item, but if not so, the flow ends here.

[QC Screen]

Figure 29:
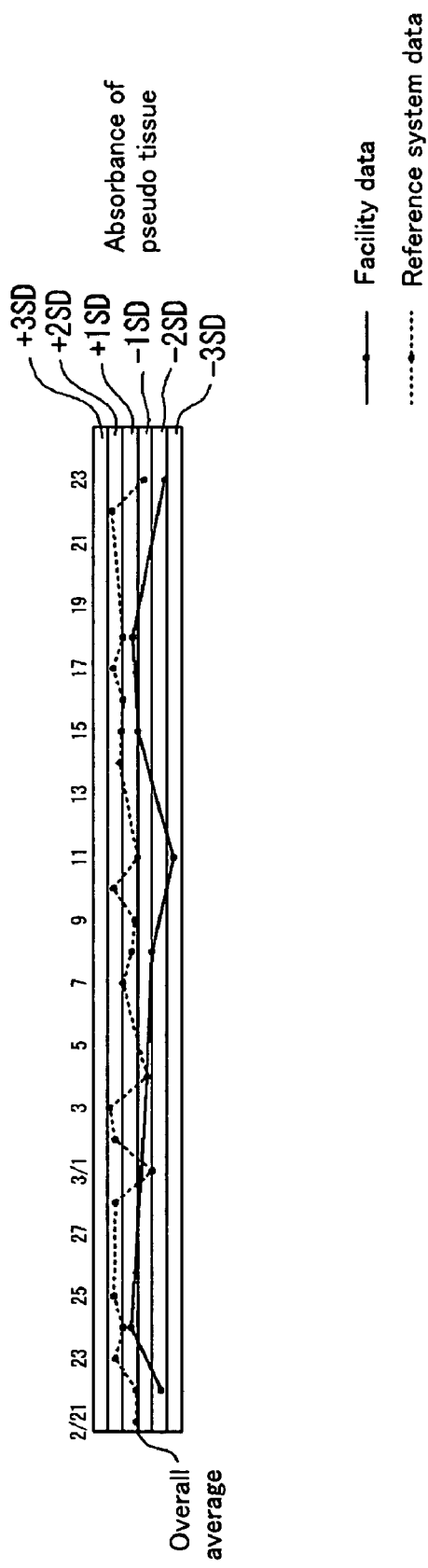
FIG. 29 is a view showing an example of QC screen in a preprocessing.
Figure 30:
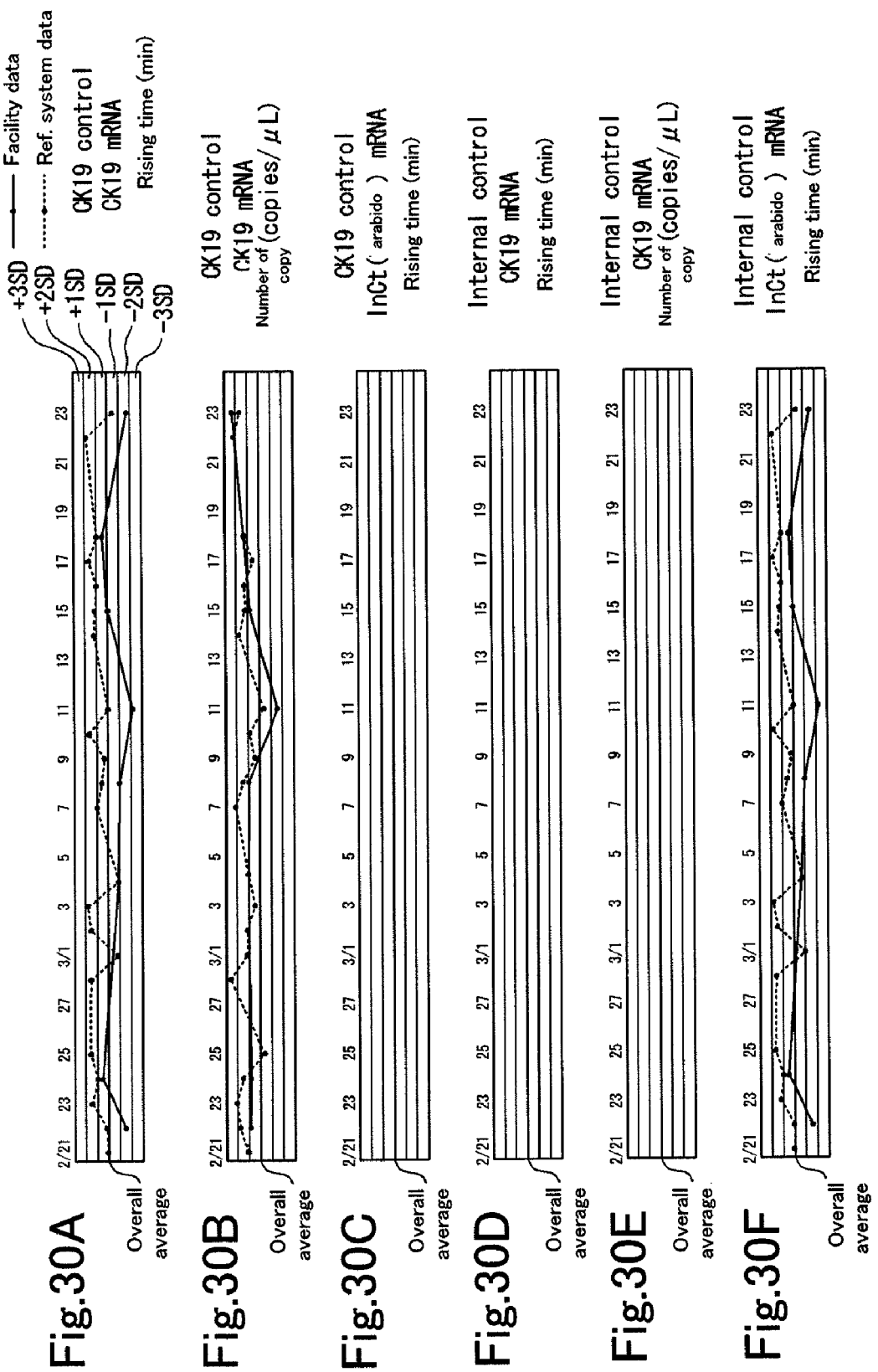
FIGS. 30A through 30F are views showing an example of QC screen in a nucleic acid detecting process.
Figure 31:
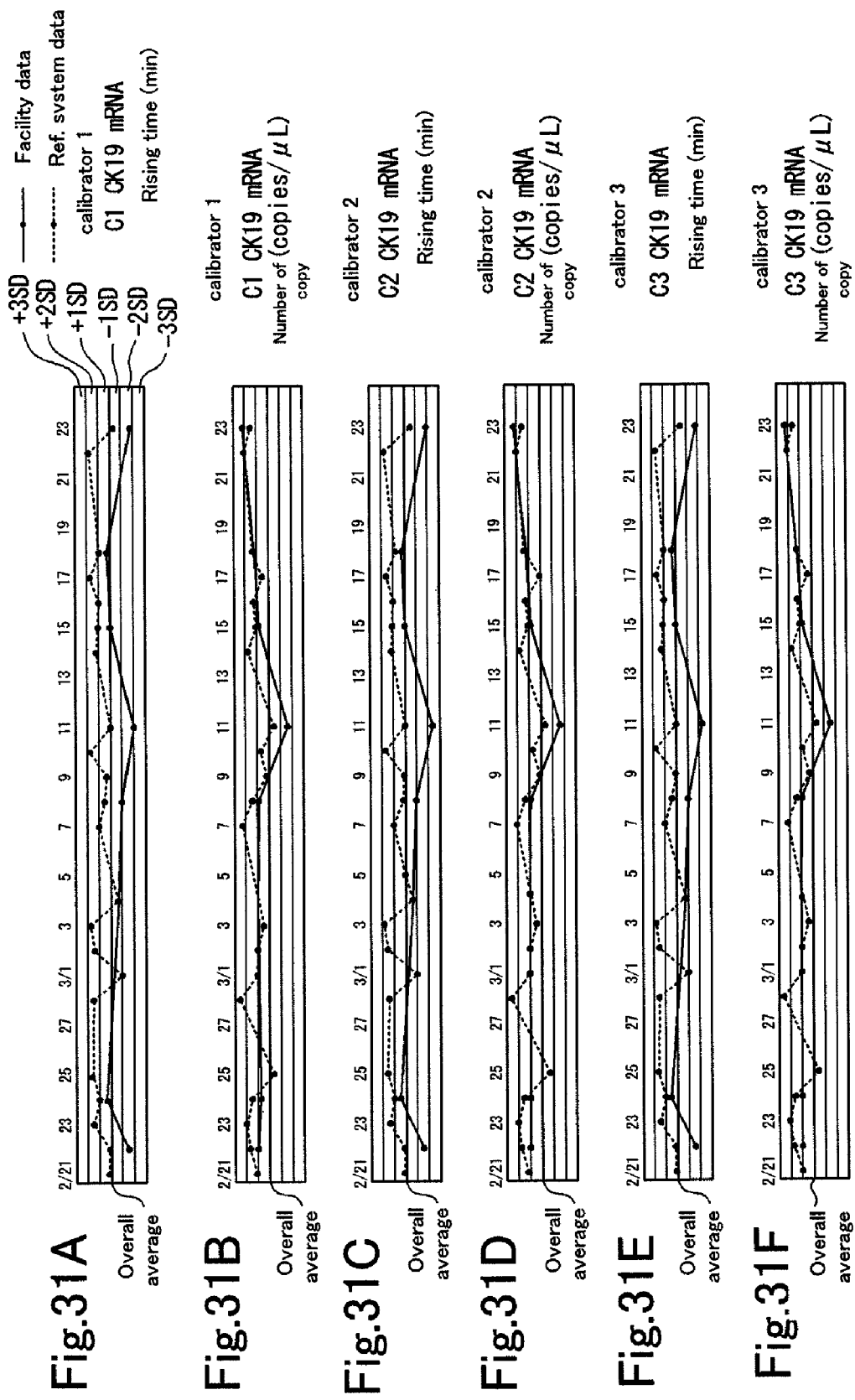
FIGS. 31A through 31F are views showing an example of QC screen in a calibration curve preparing process.

FIGS. 29 to 31 show one examples of QC screens displayed in the viewing process of the above external quality control screen. FIG. 29 shows a QC screen in the case of "QC item: preprocessing" prepared based on the absorbance statistical database DB2 and shows a difference in measurement data (facility data) of pseudo tissue that is preprocessed in the nucleic acid detecting system 2 which is to be viewed, with respect the total average of past 30 days (average of all nucleic acid detecting systems which are objects of the external quality control service). In FIG. 29, a difference in measurement data of the reference system 2*a* with respect to the total average is also shown.

In brief, in the QC screen of FIG. 29, the center horizontal axis represents an average of all nucleic acid detecting systems which are objects of the service, and the solid kinked lines represent measurement data of pseudo tissue of the nucleic acid detecting system having the device ID contained in the QC screen viewing request. In this QC screen, the range from 1SD to 3SD is shown. At the point where the measurement data of the date and time is deviated from the reference value (for example, 3SD) selected by a particular facility, it is determined that preprocessing is not properly executed, so that such point is displayed, for example, in red (not shown) for the purpose of distinction from other measurement data. The dotted kinked lines represent measurement data of pseudo tissue of the reference system 2*a*.

FIGS. 30A through 30F shows a QC screen in the case of "QC item: nucleic acid detecting process", prepared based on the quality control statistical database DB4. FIG. 30A is a QC screen showing rising time of CK19 in CK19 control, FIG. 30B is a QC screen showing CK19 copy number in CK19 control, FIG. 30C is a QC screen showing rising time of arabido in CK19 control, FIG. 30D is a QC screen showing rising time in CK19 of Internal (arabido) control, FIG. 30E is a QC screen showing CK19 copy number in Internal (arabido) control, FIG. 30F is a QC screen showing rising time of arabido in Internal (arabido) control.

The QC screen in FIGS. 30A through 30F shows a difference in measurement data (facility data) of control substance in the nucleic acid detecting system 2 which is an object to be viewed, with respect the total average of past 30 days, as well as a difference in measurement data of the reference system 2*a*.

That is, in the QC screen of FIGS. 30A through 30F, the center horizontal axis represents an average of all nucleic acid detecting systems which are objects of the service, and the solid kinked lines represent measurement data of control substance of the nucleic acid detecting system having the device ID contained in the QC screen viewing request. In this QC screen, the range from 1SD to 3SD is shown. At the point where the measurement data of the date and time is deviated from the reference value (for example, 3SD) selected by a particular facility, it is determined that the nucleic acid detecting process is not properly executed, so that the point is displayed, for example, in red (highlighted) for the purpose of distinction from other measurement data. The dotted kinked lines represent measurement data of control substance of the reference system 2*a*.

FIGS. 31A through 31F show a QC screen in the case of "QC item: calibration curve preparing process", prepared based on the quality control statistical database DB4. FIG. 31A is a QC screen showing rising time of CK19 of calibrator C1, FIG. 31B is a QC screen showing CK19 copy number in calibrator C1, FIG. 31C is a QC screen showing rising time of CK19 in calibrator C2, FIG. 31D is a QC screen showing CK19 copy number in calibrator C2, FIG. 31E is a QC screen showing rising time of CK19 in calibrator C3, and FIG. 31F is a QC screen showing CK19 copy number in calibrator C3.

FIGS. 31A through 31F show a difference in measurement data (facility data) of calibrators C1, C2, C3 in the nucleic acid detecting system 2 which is an object to be viewed, with respect the total average of past 30 days, as well as a difference in measurement data of the reference system 2*a*.

That is, in the QC screen of FIGS. 31A through 31F, the center horizontal axis represents an average of all nucleic acid detecting systems which are objects of the service, and the solid kinked lines represent measurement data of calibrator of the nucleic acid detecting system having the device ID contained in the QC screen viewing request. In this QC screen, the range from 1SD to 3SD is shown. At the point where the measurement data of the date and time is deviated from the reference value (for example, 3SD) selected by a particular facility, it is determined that the nucleic acid detecting process is not properly executed, so that the point is displayed, for example, in red (highlighted) for the purpose of distinction from other measurement data. The dotted kinked lines represent measurement data of calibrator of the reference system 2*a*.

[Analyte Measuring Processing]

Figure 32:
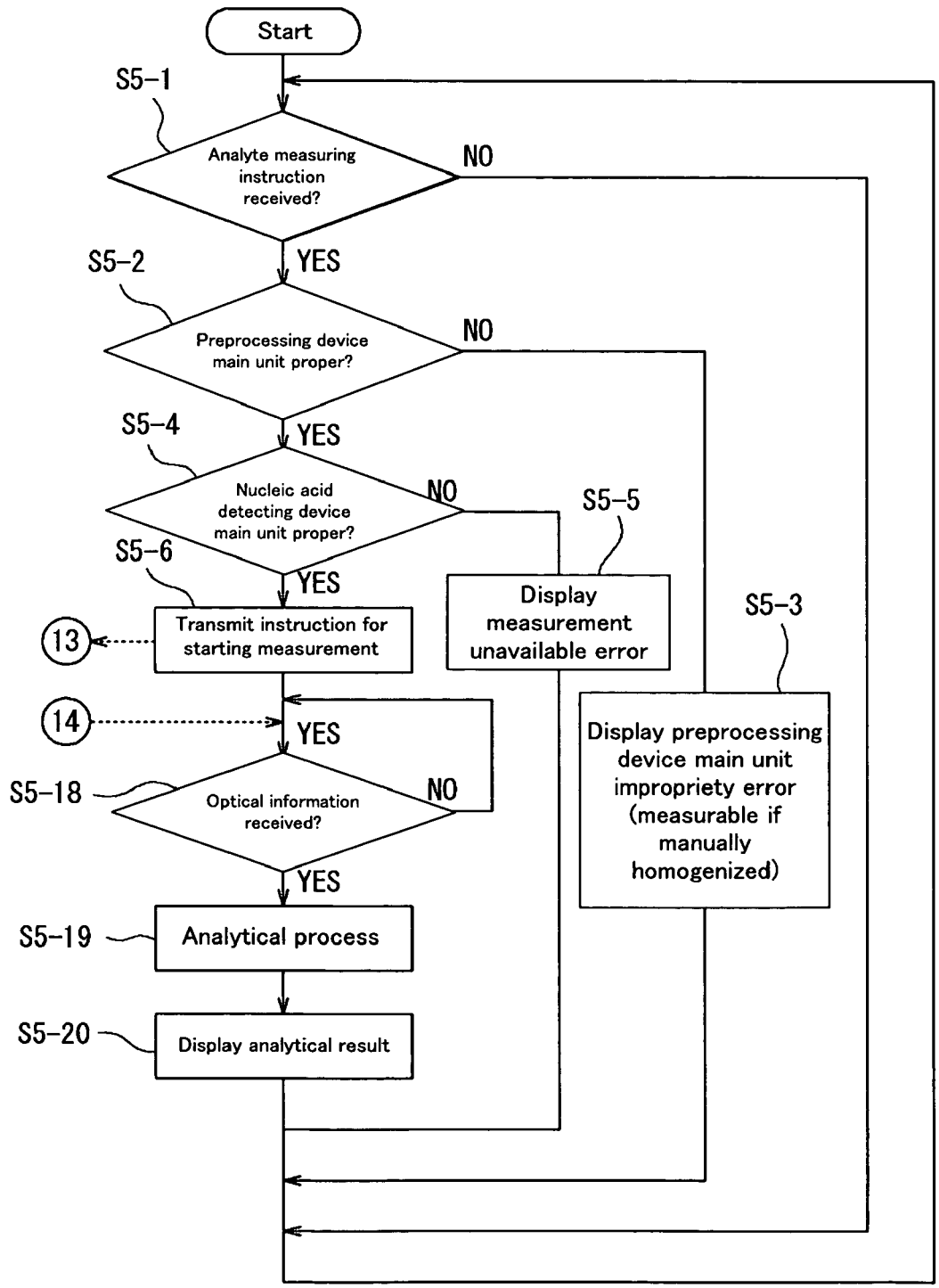
FIG. 32 is a flowchart showing an analyte measuring processing in the personal computer 6.
Figure 33:
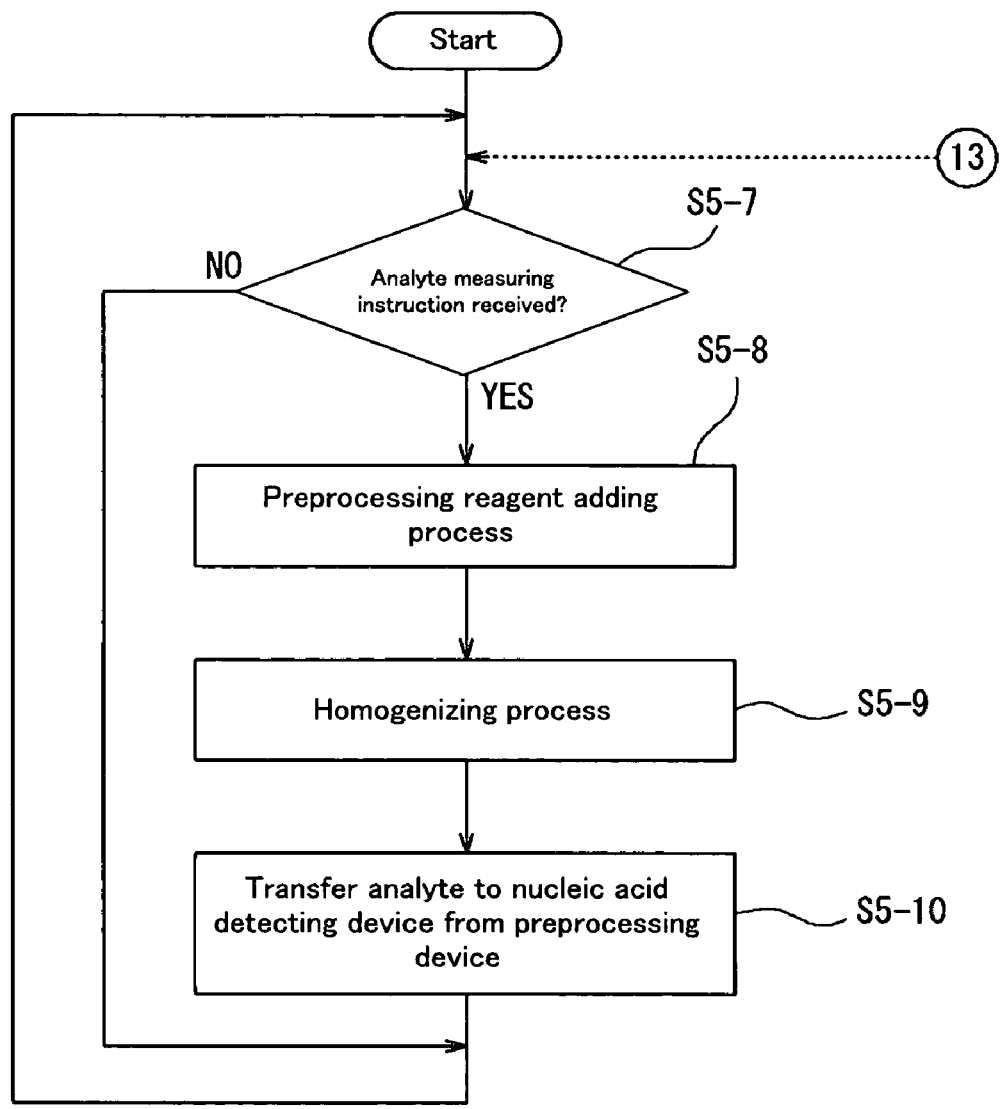
FIG. 33 is a flowchart showing an analyte measuring processing in the preprocessing device.
Figure 34:
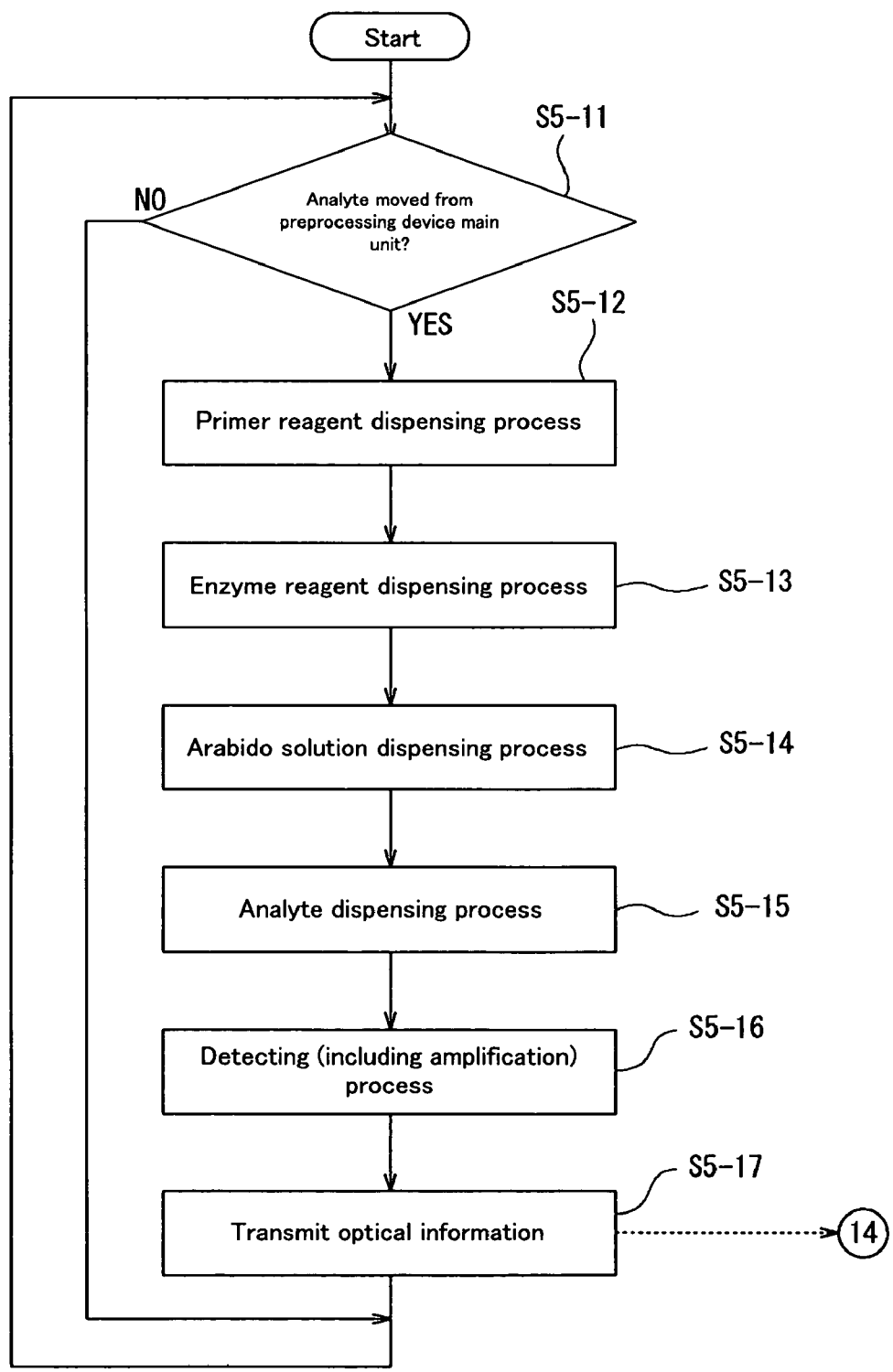
FIG. 34 is a flowchart showing an analyte measuring processing in the nucleic acid detecting device.

FIGS. 32 to 34 show processings when the nucleic acid detecting system 1 practically measures an analyte such as lymph node. First, in order to examine a tissue (lymph node) excised in a surgery for breast cancer or the like, a user (e.g., staff of hospital) inputs an instruction for analyte measurement on the personal computer 6. Upon reception of this input (Step S5-1: see FIG. 32), the personal computer 6 determines whether the preprocessing device main unit 5 properly operates or not based on the QC result of preprocessing stored in the personal computer 6 (Step S5-1).

When the preprocessing is improper, an error display notifying that the preprocessing device main unit 5 does not properly operates is made, and the flow ends without conducting measurement by the system 2 (Step S5-3). However, in the case where a manual preprocessing (homogenization) is sufficiently reliable without using the preprocessing device main unit 5, measurement at the nucleic acid detecting device main unit 101 should be permitted. Therefore, in the case where the user makes an input indicating manual preprocessing (manual homogenization) on the personal computer 6, the personal computer 6 allows for the later-described process in the nucleic acid detecting device main unit 101 in FIG. 34 while preventing the preprocessing device main unit 5 from conducting the later-described preprocessing in FIG. 33, when the nucleic acid detecting process in the nucleic acid detecting device main unit 101 is properly executed, and when the calibration curve preparing process is properly executed as is necessary.

Even when the preprocessing device main unit 5 operates properly, the personal computer 6 makes a measurement unavailable error display if the nucleic acid detecting process and the calibration curve preparing process as is necessary are not properly executed, and the flow ends without conducting measurement by the system 2 (Step S5-5).

On the other hand, when preprocessing device main unit 5 properly operates, and the nucleic acid detecting process of nucleic acid detecting device main unit 101 is properly executed and the calibration curve preparing process is properly executed as is necessary (Step S5-4), it is determined that the whole of the nucleic acid detecting system 2 operates properly, and an instruction signal for start of analyte measurement is transmitted to the preprocessing device main unit 5 (Step S5-6).

Upon reception of the instruction signal for start of analyte measurement (Step S5-7: see FIG. 33), the preprocessing device main unit 5 conducts a preprocessing reagent adding process (Step S5-8) to the analyte, and a homogenization process (Step S5-9) to prepare a measuring analyte. The prepared measuring analyte is transferred to the nucleic acid detecting device main unit 101 from the preprocessing device main unit 5 (Step S5-10).

When the nucleic acid detecting device main unit 101 detects that the measuring analyte (sample) is transferred from the preprocessing device main unit 5 (Step S5-11), a primer reagent dispensing process (Step S5-12), an enzyme reagent dispensing process (Step S5-13), an arabido solution dispensing process (Step S5-14), and an analyte (sample) dispensing process (Step S5-15) are conducted on the sample, and detection process is conducted while allowing for amplification by warming (Step S5-16), whereby optical information of the sample is obtained.

Then the nucleic acid detecting device main unit 101 transmits the obtained optical information to the data processing device 6 (Step S5-16).

Upon reception of the optical information (Step S5-18: see FIG. 32), the data processing device 6 calculates amplification rising time of CK19, and conducts an analytical process for calculating quantity (copy number) of target gene from the CK19 amplification rising time based on the rising time of arabido and the calibration curve prepared in advance.

The calculated quantitative data (measurement data) of the target gene is screen-displayed by a display unit of the data processing device 6 or by other display unit. The data processing device 6 produces a qualitative determination result for supporting diagnosis as shown in FIG. 8, bases on the measurement data (amplification rising time of CK19, copy number) and screen-displays it by a display unit of the data processing device 6 or by other display unit.

Thus the physician performing the surgery can rapidly make a diagnosis based on the displayed result, and determines a region of dissection. Additionally, since the personal computer (data processing device; controller) 6 does not permit measurement by the system 2 unless each process of the system 2 is determined as being properly executed by the external quality control, the measurement result of the system 2 has high reliability.

Furthermore, since the external quality control of the system 2 is performed on-line, the external quality control per se can be rapidly executed, so that even when rapidity is required, for example, in the case of intraoperative diagnosis, highly reliable measurement results can be obtained rapidly.

Second Embodiment

The overall configuration of the external quality control system according to the present embodiment is as same as that shown in FIG. 1. As the preprocessing device, the one shown in FIGS. 2 and 3 is used. Since configuration and operation of the nucleic acid detecting system differs from the first embodiment in that β-actin is measured instead of arabido, explanation will be made briefly with reference to FIGS. 4 and 5.

First, the pipette having moved from the preprocessing device main unit 5 injects a preprocessed sample into the sample container 22 placed in a sample container placing hole 21a of a sample container base 21.

In a primer reagent container placing hole 31a and an enzyme reagent container placing hole 31b on the front left side of a reagent container placing part 30, a primer reagent container 32a containing a primer reagent for CK19 (cytokeratin 19) and an enzyme reagent container 32b containing an enzyme reagent are respectively placed. In a primer reagent container placing hole 31a on the front right side of the reagent container placing part 30, a primer reagent container 32a containing a primer reagent for β-actin is placed. In a β-actin container placing hole 31d on the front right side, a β-actin solution container 32d containing a predetermined amount of β-actin is placed.

In a recess (not shown) of a chip placing part 40, two racks 42 each accommodating 36 disposable pipette chips 41 are fitted. Also in two detection cell placing holes in a reaction part 61 of each reaction detecting block 60a, two cell portions 66a of a detection cell 65 are placed.

When operation of the nucleic acid detecting device main unit 101 starts in this condition, first, an arm portion 11 of a dispensing mechanism part 10 moves to the chip placing part 40 from its initial position, and then in the chip placing part 40, two syringe portions 12 of the dispensing mechanism part 10 are moved downward. As a result, tip ends of nozzle portions of the two syringe portions 12 are pressed into upper openings of the two pipette chips 41, so that the pipette chips 41 are automatically attached to the tip ends of the nozzle portions of the two syringe portions 12. Then after the two syringe portions 12 have been moved upward, the arm portion 11 of the dispensing mechanism part 10 is moved in the X-axial direction toward above the two primer reagent containers 32a respectively containing primer reagents for CK19 and β-actin, placed on the reagent container placing base 31. Then the two syringe portions 12 are moved downward so that the tip ends of the two pipette chips 41 attached to the nozzle portions of the two syringe portions 12 are respectively inserted into the liquid surfaces of the primer reagents for CK19 and β-actin in the two primer reagent containers 32a. Then the primer reagents for CK19 and β-actin in the two primer reagent container 32a are suctioned by pumps of the syringe portions 12.

After the two syringe portions 12 have moved upward following suction of the primer reagents, the arm portion 11 of the dispensing mechanism part 10 is moved above a reaction detecting block 60a situated in the innermost position from front face (innermost from the front face of the device). In this case, the arm portion 11 of the dispensing mechanism part 10 is moved without passing above other second to fifth reaction detecting blocks 60a counted from the innermost one. In the innermost reaction detecting block 60a, the two syringe portions 12 are moved downward, so that the two pipette chips 41 attached to the nozzle portions 12a of the two syringe portions 12 are respectively inserted into the two cell portions 66a of the detection cell 65. Then two primer reagents for CK19 and β-actin are respectively discharged into two cell portions 66a by means of pumps of the syringe portions 12 (primer reagent dispensing process).

Then the pipette chips 41 are disposed, and after two new pipette chips 41 are automatically attached to the tip ends of the nozzle portions of the two syringe portions 12, an enzyme reagent within the enzyme reagent container 32b is discharged into two cell portions 66a of the detection cell 65 in a similar manner as described above (enzyme reagent dispensing process).

Then, also in a similar manner, the β-actin solution within the β-actin solution container 32d is discharged into two cell portions 66a of the detection cell 65.

Then, also in a similar manner, the sample (measuring analyte) in the sample container 22 is discharged into two cell portions 66a of the detection cell 65 (sample dispensing process).

As a result, a sample for detection of CK19 is prepared in one of the cell portions 66a of the detection cell 65 and a sample for detection of β-actin is prepared in the other of the cell portions 66a.

After completion of discharges of the primer reagents, enzyme reagent, β-actin solution and sample into the cell portions, a lid of the detection cell 65 is closed.

After closing the lid, the liquid temperature in the detection cell 65 is raised from about 20° C. to about 65° C. by means of a Peltier module of the reaction part 61 for amplifying a target gene (CK19) and β-actin by the LAMP method.

Then the white turbidity due to magnesium pyrophosphate generated with amplification is detected by turbidimetry. Concretely, a light beam having a diameter of about 1 mm is emitted from a LED optical source 62a of the turbidity detecting part 62 to the cell portion 66a of the detection cell 65 (measurement data acquiring part) in amplification reaction via a light emitting groove of the reaction part 61. Then the emitted light is received by a photodiode light receiving part 62b.

In this manner, the liquid turbidity in the cell portion 66a of the detection cell 65 in amplification reaction is detected (monitored) in real time (detection process).

Measurement data of CK19 and measurement data of β-actin measured at the photodiode light receiving part 62b (measurement data acquiring means) are transmitted to data processing device 6 by the transmitter (not shown) possessed by the nucleic acid detecting device main unit 101.

As a result, in the data processing device 6, when the horizontal axis represents time, and the vertical axis represents turbidity (O.D.: Optical Density), measurement data of CK19 as shown in FIG. 6 is obtained. From this measurement data of CK19, amplification rising time which is a time required for the target gene (CK19) in the sample to rapidly increase the copy numbers is detected by comparing the turbidity with a predetermined threshold.

On the other hand, the data processing device 6 also prepares measurement data of β-actin in which the horizontal axis represents time and the vertical axis represents turbidity from the measurement data of β-actin in the same manner as described above, and acquires amplification rising time of β-actin based on the measurement data.

The calibration curve shown in FIG. 7 is a curve in which the horizontal axis represents amplification rising time and the vertical axis represents copy number [copy number/μL] of target gene (CK19), and in general, the shorter the amplification rising time, the higher the concentration of the target gene.

By fitting the obtained amplification rising time of CK19 to the calibration curve prepared from the measurement result of calibrator of CK19 as shown in FIG. 7, quantity (copy number) of target gene (CK19) is calculated.

Similarly, a calibration curve (provided that the horizontal axis represents amplification rising time and the vertical axis represents copy number [copy number/μL] of β-actin) as shown in FIG. 7 is prepared in advance from the measurement result of calibrator of β-actin, and quantity (copy number) of β-actin is calculated by fitting the amplification rising time of β-actin to this calibration curve.

Based on this copy number of β-actin, the data processing device 6 corrects copy number of CK19. β-actin which is also called "house keeping gene" is expressed in a certain amount in any cells, so that the influence of the quantity of analyte to be amplified on measurement result can be removed by such correction.

It is to be noted that correction based on copy number of β-actin is not necessarily essential, and copy number of β-actin may be used for knowing that an analyte is properly injected into the detection cell 65. In other words, since β-actin is expressed in a certain amount in any cells, if copy number of β-actin falls within a predetermined range, it means that an analyte is properly injected into the detection cell 65, whereas if the copy number of β-actin does not fall within the predetermined range, it means that an analyte is not properly injected into the detection cell 65.

The calculated quantitative data (measurement data) of target gene (CK19) is screen-displayed by a display unit of the data processing device 6 or by other display unit. The data processing device 6 determines a qualitative determination result for supporting diagnosis, from the quantitative measurement data (amplification rising time, copy number), and screen-displays it by a display unit of the data processing device or by other display unit.

Determination is made in the following manner. For example, when the number of copies is 250 or less as shown in FIG. 8, or when the turbidity fails to reach a threshold even after a predetermined time has lapsed in the measurement data shown in FIG. 6, it is determined as "ND", and when the number of copies falls within the range of 250 to $5 \times 10^3$, it is determined as "+", and when the number of copies is larger than $5 \times 10^3$, it is determined as "++". Here, qualitative degree of cancer metastasis is represented by "ND: no metastasis is detected", "+: little metastasis is detected", and "++: metastasis is detected". The system 2 determines and displays a qualitative result that is useful for supporting definite diagnosis, from the quantitative measurement data (quantity of cells derived from cancer), which allows a physician to rapidly make diagnosis during a surgery and determines a region of dissection.

The calibration curve used for acquiring copy number of β-actin is prepared in a similar manner as described in the paragraph of "External quality control of calibration curve preparing process" in the first embodiment, and quality thereof is externally controlled.

Further, in the second embodiment, since external quality control of the nucleic acid detecting process is different from that of the first embodiment, explanation will be given on the external quality control.

When external quality control of the nucleic acid detecting device 101 is conducted, a quality control analyte for nucleic acid detection (hereinafter, referred to as simply "control solution") instead of the normal measuring analyte is measured by means of the nucleic acid detecting device main unit 101.

As the control solution, two controls are used: positive control containing a predetermined amount of CK19 which is a target nucleic acid and containing a predetermined amount of β-actin and negative control lacking both CK19 and β-actin.

First, prior to an external quality control processing (control solution measuring process), a sample container 22 containing positive control, and a sample container 22 containing negative control are placed in the sample container base 21 of the nucleic acid detecting device main unit 101.

Then a user (e.g., staff of hospital) inputs a start instruction via the input unit such as keyboard and mouse of the personal computer 6 in the system 2 so as to start the external quality control of the nucleic acid detecting device main unit 101, and upon reception of the instruction (Step S2-1: see FIG. 16), the personal computer (control unit) 6 transmits a measurement starting instruction to the nucleic acid detecting device 101 (Step S2-2).

Upon reception of a signal instructing start of measurement (Step S2-3: see FIG. 17), the nucleic acid detecting device main unit 101 conducts a primer reagent dispensing process (Step S2-4), an enzyme reagent dispensing process (Step S2-5), and a control solution dispensing process (Step S2-6) which dispenses the positive control solution in the sample container 22 into one of the cell portions 66a of the detection cell 65, and the negative control solution into the other of the cell portions 66a.

Thereafter, the nucleic acid detecting device main unit 101 amplifies the target nucleic acid (CK19) and β-actin according to the LAMP method by warming the liquid temperature in the detection cell 65 from about 20° C. to about 65° C., and conducts a detection process by which the liquid turbidity in each cell portion 66a of the detection cell 65 in the amplification reaction is detected (monitored) in real time by the turbidity detecting part 62 (Step S2-7).

Then the nucleic acid detecting device main unit 101 transmits the detected optical information (measurement data of CK19 and measurement data of β-actin) to the personal computer 6 (Step S2-8).

Upon reception of the optical information (liquid turbidity) from the nucleic acid detecting device main unit 101 (Step S2-9: see FIG. 16), the personal computer 6 executes an analytical process for the optical information (Step S2-10). In the analytical process, amplification rising time of CK19, copy number of CK19, amplification rising time of β-actin, and copy number of β-actin are calculated.

As described above, amplification rising times of CK19 and β-actin are calculated as times required for the liquid turbidity obtained as optical information to exceed a predetermined value, and copy numbers of CK19 and β-actin are respectively calculated from the amplification rising times of CK19 and β-actin based on the calibration curve prepared in advance from a measurement result of a calibrator. In measurement of the control solution, correction of copy number of CK19 based on copy number of β-actin as described above is not conducted.

The above analytical process is executed for each of the two control substances.

That is, in the analytical process, rising time of CK19 (target nucleic acid) and rising time of β-actin when positive control is measured, as well as rising time of CK19 (target nucleic acid) and rising time of β-actin when negative control is measured are calculated, and copy numbers of CK19 and β-actin are calculated for each of positive control and negative control based on the rising times of CK19 and β-actin.

The analytical result (measurement data) is transmitted from the personal computer 6 to the server 1 (Step S2-11). Upon reception of analytical result (measurement data) (Step S2-12: see FIG. 18), the server 1 stores the measurement data in the quality control database DB3 (Step S2-13).

The server 1 also conducts statistical process on plural measurement data transmitted from personal computers 6 of a plurality of nucleic acid test systems 2 installed in different facilities. Concretely, based on the measurement data transmitted from the systems 2 (personal computer 6) installed in the plurality of facilities, daily average and standard deviation 1SD are determined for each measurement item (Step S2-14).

The server 1 also determines 2SD which is twice the standard deviation 1SD and 3SD which is three times the standard deviation 1SD. These daily averages of measurement data of 1SD, 2SD, 3SD are stored in the quality control statistical database DB4 of the server 1. The quality control statistical database DB4 also stores measurement data of reference system 2a.

Further, upon reception of measurement data, the server 1 determines whether the nucleic acid detecting process is properly executed or not based on the average, and 1SD, 2SD or 3SD calculated in Step S2-14 (Step S2-15).

More specifically, the server 1 determines whether the nucleic acid detecting process is properly executed or not based on the average and standard deviation 1SD, 2SD or 3SD of measurement data received in a past preset time (for example, past 24 hours) for every measurement data.

Each of 1SD, 2SD and 3SD is a potential reference value for determining whether the received measurement data is proper or not, and decision of which one of 1SD, 2SD and 3SD is to be used rests with a particular facility, and the selected reference value is used for determination.

Determination (QC (Quality Control) result determination) may be made as "proper" if average of received copy number of CK19 falls within the range of $4.1\times10^3 \pm 2.6\times10^3$ and "improper" if it does not fall within the range of $4.1\times10^3 \pm 2.6\times10^3$, assuming that 2SD is selected as a reference value, an average of copy number of CK19 received in a past preset time is $4.1\times10^3$, and standard deviation ($\times 2$)2SD is $2.6\times10^3$, for example. Determinations for rising time of CK19 and rising time of β-actin are also conducted in a similar manner.

The statistical processing result and the determination result (QC results) produced by the server 1 is transmitted to the personal computer 6 of the system 2 from which the measurement data of absorbance is transmitted (Step S2-16). Upon reception of the data of QC result (statistical processing result and the determination result) (Step S2-17, see FIG. 16), the personal computer 6 executes a process of storing the QC results in a storing means such as hard disc (Step S2-18).

Through the above processing, the nucleic acid detecting system 2 is provided with information about whether the nucleic acid detection process is properly executed or not.

The present invention is not limited to the foregoing two embodiments.

For example, the nucleic acid detecting system 2 may not have the preprocessing unit 50 of the preprocessing device main unit 5. That is, in the system 2, the preprocessing unit 50 may be omitted, and the system 2 may have the measuring unit 51 for measuring absorbance of a preprocessed analyte, the nucleic acid detecting device main unit 101, and the data processing device 6, and measure a manually preprocessed analyte in the measuring unit 51.

Alternatively, the entire preprocessing device main unit 5 may be omitted, and absorbance of a manually preprocessed analyte may be measured with the use of the detecting part 62 of the nucleic acid detecting device main unit 101. When external quality control processing for the nucleic acid detecting device main unit 101 is designed to conduct both measurement of preprocessed analyte and measurement of control solution as described above, the nucleic acid detecting device main unit 101 preferably has a function of switching between these measurements.

When the preprocessing unit 50 is omitted as described above, a user can know how much the preprocessing (homogenization) is needed from the quality control result of preprocessing, and realize that an analyte can be homogenized in preprocessing similarly to homogenization of pseudo tissue for preprocessing when the quality control result is proper.

As the preprocessing unit 50 of the preprocessing device, a device that executes a method descried in U.S. Pat. No. 6,562,568 may be used without being limited to those disclosed in the above embodiments.

Additionally, in the above embodiments, the preprocessing device main unit 5 and the nucleic acid detecting device main unit 101 are connected to a network via the data processing device 6, however, these need not use the data processing device 6 to be connected to a network. The preprocessing device main unit 5 and the nucleic acid detecting device main unit 101 need not be integrally formed, and may be implemented by separate instruments. When these device main units 5, 101 are configured by separate instruments, movement of analyte to the preprocessing device main unit 5 from the detecting device 101 may be conducted manually, or by means of a mechanism for movement provided separately.

In the above embodiments, the preprocessing device main unit 5 and the nucleic acid detecting device main unit 101 are respectively connected to the data processing device 6, however, the preprocessing device main unit 5 may be connected to the nucleic acid detecting device main unit 101, and the nucleic acid detecting device main unit 101 may be connected to the data processing device 6. In this case, data transmission/reception between the preprocessing device main unit 5 and the data processing device 6 is achieved via the nucleic acid detecting device main unit 101.

Furthermore, the measuring unit 51 of the preprocessing device main unit 5 may be omitted. In this case, absorbance of the analyte preprocessed at the preprocessing unit 50 may be measured using the detecting part 62 of the nucleic acid detecting device main unit 101.

In the above embodiments, the preprocessing device main unit 5 and the nucleic acid detecting device main unit 101 are respectively connected to the data processing device 6, however, the function of the data processing device 6 may be incorporated into the preprocessing device main unit 5 to form an integrated unit, or the function of the data processing device 6 may be incorporated into the nucleic acid detecting device main unit 101 to form an integrated unit, or the preprocessing device main unit, the nucleic acid detecting device main unit 101 and the data processing device 6 may be integrated.

In the above first embodiment, CK19 control and arabido control are used; however, arabido control may be omitted.

In the above second embodiment, positive control and negative control are used, however, positive control may contain a predetermined amount of CK19 and lack β-actin, an negative control may lack both CK19 and β-actin. In such a case, the nucleic acid detecting system 2 may omit measurement of β-actin and correction based on copy number of β-actin.

Furthermore, in the above second embodiment, positive control contains a predetermined amount of β-actin, however, glyceraldehyde-3-phosphate dehydrogenase (GAPDH), β2-microglobulin, or hypoxanthine phosphoribosyltransferase 1 (HPRT 1) may be used in place of β-actin. In such a case, the measurement items for analyte may be as same as those for the gene contained in the positive control analyte, and rising time or copy number of CK19 may be corrected based on the rising time or copy number of such gene.

β-actin, GAPDH, β2-microglobulin, and HPRT 1 are also called "house keeping gene", and are commonly expressed in certain amounts in a number of tissues and cells. Therefore, by measuring such a house keeping gene, it is possible to determine that a certain amount of cancer cells which are objects of measurement is contained in the measurement analyte. Further, in comparing expression amounts of nucleic acid in different samples, quantification is achieved by amplification of a target nucleic acid and fitting into a calibration curve. Since RNAs should be extracted with the same efficiency from the samples of the same number of cells and target RNAs should be amplified with the same efficiency in order to realize accurate comparison, it is advantageous to correct RNA amounts between the samples based on a relative expressed amount of a standard gene. For achieving this, a house keeping gene such as β-actin is examined as a standard gene, and correction of RNA amounts between samples is conducted, and thereby reliability of measurement result is improved.

In the above embodiments, separate quality control analytes are used for the quality control analyte for preprocessing and for the quality control analyte for nucleic acid detection, however, a common quality control analyte may be used for preprocessing and for nucleic acid detection. In such a case, common quality control analytes may be used for preprocessing and nucleic acid detection, or a quality control analyte having experienced preprocessing and absorbance measurement by the preprocessing device main unit 5 may be transferred to the nucleic acid detecting device main unit 101, and the transferred quality control analyte may be used as a quality control analyte for nucleic acid detection.

What is claimed is:

1. An external quality control method, using an external quality control computer and a plurality of nucleic acid detecting systems connected to the external quality control computer via a network, each of the nucleic acid detecting systems comprising a preprocessing device for preparing an assay sample by preprocessing a patient sample and a nucleic acid detecting device for detecting a target nucleic acid in the assay sample prepared by the preprocessing device, the method comprising:

at the preprocessing device of the nucleic acid detecting system, performing a preprocessing operation on a quality control sample to prepare an assay sample for quality control by homogenizing a quality control sample in a homogenization reagent, wherein the quality control sample contains a predetermined amount of nucleic acid and/or a predetermined amount of cells;

at the nucleic acid detecting system, measuring the assay sample for quality control to obtain measurement data;

from the nucleic acid detecting system, providing the measurement data to the external control computer over the network;

at the quality control computer, calculating an average value and a standard deviation of measurement data which were provided from the nucleic acid detecting systems;

at the quality control computer, determining whether the preprocessing operation of the preprocessing device is properly performed by evaluating the received measurement data on the basis of the average value and the standard deviation; and from the quality control computer, providing the determination result to the nucleic acid detecting system, wherein in the nucleic acid detecting system, the preprocessing device prepares an assay sample for detection by performing the preprocessing operation on a patient sample, and wherein the nucleic acid detecting device amplifies a target nucleic acid in a mixture of the assay sample for detection and a primer reagent and detects the target nucleic acid in the mixture.

2. The external quality control method of claim 1, wherein the preprocessing quality control samples is a solid artificial tissues comprising a predetermined amount of nucleic acid and/or predetermined amount of cells and a holder for holding the nucleic acid and/or the cells.

3. The external quality control method of claim 1, wherein the measuring the assay sample for quality control comprises obtaining optical information obtained by irradiating light of the assay sample for quality control.

4. The external quality control method of claim 1, further comprising from the external quality control computer, providing a screen displaying the determined average value and the determined standard deviation.

5. The external quality control method of claim 1, wherein the average value is calculated from the measurement data which were provided in a predetermined period, and
the standard deviation is calculated by statistically evaluating the measurement data which were provided and stored in the predetermined period.

6. An external quality control method, using an external quality control computer and a plurality of nucleic acid detecting devices connected to the external quality control computer via a network, comprising:
at the nucleic acid detecting device, measuring a calibrator which contains a predetermined amount of a target nucleic acid to obtain measurement data, wherein the nucleic acid detecting device measures a calibrator by (i) amplifying the target nucleic acid in the calibrator and (ii) measuring a time taken until the target nucleic acid are amplified up to predetermined amount, and the measurement data comprises the measured time;
from the nucleic acid detecting device, providing the measurement data to the external control computer over the network;
at the external quality control computer, calculating an average value and a standard deviation of measurement data which were provided from the nucleic acid detecting devices;
at the external quality control computer, determining whether the nucleic acid detecting device measures the calibrator properly by evaluating received measurement data on the basis of the average value and the standard deviation; and
from the external quality control computer, providing the determination result to the nucleic acid detecting device.

7. An external quality control method, using an external quality control computer and a plurality of nucleic acid detecting devices connected to the external quality control computer via a network, comprising:
at the nucleic acid detecting device, measuring a calibrator which contains a predetermined amount of a target nucleic acid to obtain measurement data, wherein the nucleic acid detecting device measures a calibrator by (i) amplifying the target nucleic acid in the calibrator, (ii) measuring a time taken until the target nucleic acid are amplified up to predetermined amount, (iii) generating a calibration curve on the basis of the predetermined amount of the target nucleic acid in the calibrator and the measured time, and (iv) converting the measured time into an amount of the target nucleic acid in the calibrator by using the generated calibration curve, and the measurement data comprises the converted amount of the target nucleic acid in the calibrator;
from the nucleic acid detecting device, providing the measurement data to the external control computer over the network;
at the quality control computer, calculating an average value and a standard deviation of measurement data which were provided from the nucleic acid detecting devices;
at the quality control computer, determining whether the generated calibration curve is proper or not by evaluating the received measurement data on the basis of the average value and the standard deviation; and
from the quality control computer, providing the determination result to the nucleic acid detecting device.

8. A preprocessing device for preparing an assay sample for detection by a nucleic acid detecting device, comprising:
a preprocessing section for performing a preprocessing operation, the preprocessing section comprising a reagent dispenser for dispensing a homogenization reagent; a homogenizer for homogenizing a sample in the homogenization reagent; and a pipette for aspirating an assay sample from the homogenate;
a measurement section for measuring the assay sample to obtain measurement data;
a communicating section for communicating with an external quality control computer via a network; and
a display section,
wherein a patient sample is preprocessed by the preprocessing section to prepare an assay sample for detection, and the nucleic acid detecting device amplifies a target nucleic acid in the assay sample for detection in a mixture of the assay sample for detection and a primer reagent and detects the target nucleic acid in the mixture,
wherein a quality control sample which contains a predetermined amount of nucleic acid and/or a predetermined amount of cells is preprocessed by the preprocessing section to prepare an assay sample for quality control sample, the measurement section measures the assay sample for quality control to obtain a measurement data, and the communicating section transmits the measurement data to the external quality control computer,
wherein the external quality control computer executes operations comprising:
receiving the transmitted measurement data;
by statistical evaluation, calculating an average value and a standard deviation of stored measurement data;
determining whether a preprocessing operation of the preprocessing device is properly performed by evaluating the received measurement data on the basis of the average value and the standard deviation; and
providing the determination result to the preprocessing device,
and wherein the display section is enabled to display the provided determination result.

* * * * *